(12) United States Patent
Kido et al.

(10) Patent No.: US 8,841,237 B2
(45) Date of Patent: Sep. 23, 2014

(54) TRANSCRIPTION CHIP

(75) Inventors: Hiroshi Kido, Tokushima (JP);
Mineyoshi Hiyoshi, Tokushima (JP);
Miwa Bando, Itano-gun (JP); Moritoshi Kinoshita, Itano-gun (JP); Yoji Fukuda, Myodo-gun (JP); Hiroshi Mizuguchi, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/417,862

(22) Filed: Mar. 12, 2012

(65) Prior Publication Data

US 2013/0023429 A1 Jan. 24, 2013

Related U.S. Application Data

(62) Division of application No. 10/556,679, filed as application No. PCT/JP2004/006796 on May 13, 2004.

(30) Foreign Application Priority Data

May 16, 2003 (JP) ................................. 2003-138395

(51) Int. Cl.
*C40B 30/04* (2006.01)
*C12Q 1/68* (2006.01)
(52) U.S. Cl.
CPC .................... *C12Q 1/6837* (2013.01)

USPC ........................................................... 506/9
(58) Field of Classification Search
None
See application file for complete search history.

(56) References Cited

FOREIGN PATENT DOCUMENTS

| JP | 2003125764 | 5/2003 |
|----|------------|--------|
| WO | 0173115 | 10/2001 |

OTHER PUBLICATIONS

Panisko et al. (Feb. 2002) Experimental Hematology vol. 30 pp. 97 to 107.*
Smith et al., "Surface Plasmon Resonance of Transcription Factor Proteins: Interactions of Bacterial Response Regulators with DNA Arrays on Gold Films", Langmuir, 19(5):1486-1492 (Mar. 2003).
Kido et al., "Application f the Gene-DIA® Diamond DNA Chip and Dvelopment of a Protein Chip", The Journal of the Institute of Electronics, Information and Communication Engineers, 85(10):725-727 (Oct. 2002).
Tsugita, "Profile of Protein Primary Structure Analysis—Using Mass Spectrometry in Particular", Pharmacia, 33(9):990-995 (1997).
Patterson, "Matrix-Assisted Laser-Desorption/Ionization Mass Spectrometric Approaches for the Identification of Gel-Separated Proteins in the 5-50 PMOL Range", Electrophoresis, 16(7):1104-1114 (1995).

* cited by examiner

*Primary Examiner* — Christian Boesen
(74) *Attorney, Agent, or Firm* — Sughrue Mion, PLLC

(57) ABSTRACT

A transcription chip comprising a substrate and, immobilized thereon, at least one polynucleotide including an element sequence to which a transcription factor can be bound.

12 Claims, 24 Drawing Sheets

| | |
|---|---|
| Sensitivity | 55% |
| LaserPower | 100% |
| Chip size | 3mm角 |
| Double-stranded DNA (PRO II) immobilization concentration | 25 μM |
| Excitation wavelength | 473nm |
| Detection filter | 535nm |
| Fluorescence detector | HITACHI CRBIO-II |
| Spot pin diameter. | 150nm |
| Spot pitch | 0.75mm |

Fig. 15

Data Set 1 Results

MS-Fit search selects 1767 entries (results displayed for top 5 matches).

Results Summary

| | MOWSE Score | #/24(%) Masses Matched | % Cov | % TIC | Mean Err ppm | Data Tol ppm | MS-Digest Index # | Protein MW (Da)/pI | Accession # | Species | Protein Name |
|---|---|---|---|---|---|---|---|---|---|---|---|
| 1 | 8.357e+004 | 7 (29) | 30.0 | 29.2 | -66.0 | 8.59 | 622012 | 41071/6.9 | 1633504 | UNREADABLE | gi|1633504|pdb|1SVC|P Chain P, Nfkb P50 Homodimer Bound To Dna |
| 2 | 4925 | 5 (20) | 15.0 | 20.8 | -61.6 | 50.4 | 1138519 | 55711/5.4 | 20271482 | MUS MUSCULUS | (BC028325) Similar to G1 to S phase transition 1 |
| 3 | 3844 | 5 (20) | 30.0 | 20.8 | -69.4 | 13.1 | 1044561 | 34876/8.1 | 4139751 | UNREADABLE | gi|4139751|pdb|1VKX|B Chain B, Crystal Structure Of The NfkB P50P65 HETERODIMER COMPLEXED To The Immunoglobulin Kb Dna |
| 4 | 3668 | 5 (20) | 29.0 | 20.8 | -69.4 | 13.1 | 1187882 | 36543/8.7 | 1942806 M | UNREADABLE | gi|1942806|pdb|1NFK|A Chain A, Structure Of The Nuclear Factor Kappa-B (Nf-Kb) P50 Homodimer |
| 5 | 2672 | 5 (20) | 29.0 | 20.8 | -62.4 | 76.1 | 222550 | 27041/6.5 | 23495361 | HOMO SAPIENS | (AB074415) brain acyl-CoA hydrolase |

Fig. 22

| | Accession | Mass | Score | Description |
|---|---|---|---|---|
| 1. | 1SVCP | 34773 | 269 | transcription factor nfkb p50 residues 2 366 mutant C62A, chain P |
| 2. | A37867 | 105304 | 255 | transcription factor NF-kappa-B 50K chain precursor - human |
| 3. | AAF35232 | 105290 | 255 | AF213884S1 NID: - Homo sapiens |
| 4. | Q86V43 | 105361 | 255 | NFKB1 protein. - Homo sapiens (Human). |
| 5. | AAA36361 | 105375 | 255 | HUMNFKB34 NID: - Homo sapiens |
| 6. | CAB94757 | 105382 | 218 | HSNFXN2 NID: - Homo sapiens |
| 7. | INF1B | 12417 | 91 | nf-kappa-b p50, chain B - human |
| 8. | CAA12618 | 7554 | 43 | IG HEAVY CHAIN VARIABLE REGION (FRAGMENT). - Homo sapiens (Human). |
| 9. | Q86VM0 | 29492 | 43 | Similar to cDNA sequence BC019776 (Fragment). - Homo sapiens (Huma |
| 10. | AAF63222 | 5045 | 42 | Immunoglobulin alpha chain (Fragment). - Homo sapiens (Human). |

TRANSCRIPTION CHIP

CROSS-REFERENCE TO RELATED APPLICATIONS

This application is a Divisional application of U.S. application Ser. No. 10/556,679, filed Jun. 29, 2007; which is a 371 of PCT/JP2004/006796, filed May 13, 2004; which claims priority from Japanese Application No. JP 2003-138395, filed May 16, 2003; the disclosures of each of which are incorporated herein by reference.

TECHNICAL FIELD

The present invention relates to a transcription chip and a method for measuring an activity of a transcription factor using the chip.

BACKGROUND ART

A DNA chip is a tool to profile gene polymorphism and variance of mRNA expression levels, and is currently used in wide research fields. Proteins which are final products obtained by translating mRNA which transfer genomic information bear momentarily changing vital phenomena. Thus, it has been believed that more useful information than the information obtained by profiling the mRNA is obtained from the protein, and techniques for proteome analysis which analyzes the protein exhaustively have been actively developed.

In such an actual circumstance, if a system where a protein is captured on a substrate and efficiently characterized is completed, it is estimated that the system will be a new technology which is superior to conventional analytical methods for the proteome using two dimensional electrophoresis or liquid chromatography in terms of scale and cost. Up to now, antibody chips have been developed as the chip which targets the proteome analysis. The antibody chip is the tool where many antibodies are immobilized on chip surfaces and amounts of antigens which interact with the immobilized antibodies, respectively are profiled. The antibody chips were developed later than DNA chips, but their practical application in the wide fields such as drug discovery, toxicity tests or pathological diagnosis in the future is anticipated because the variance of the proteins can be directly analyzed.

A transcription factor is deeply involved in cellular inflammatory response, carcinogenesis and transcription controlling factor activation because it is the protein which is bound to a region called an element sequence in an upstream region of each gene and regulates the expression of various genes. Therefore, it is very important to, at a protein level, profile various transcription factors which keep biological activity.

Conventionally, the transcription factor has been analyzed by a technique using acrylamide gel electrophoresis using a radioisotope called a gel shift assay, but the technique is problematic in throughput and safety, and it is believed that it is difficult to apply to future proteomic techniques.

The present invention intends to provide a technology to efficiently profile the transcription factor.

DISCLOSURE OF INVENTION

The present inventor has made a transcription chip where single or double-stranded DNA comprising one or more element sequences of transcription factors are immobilized on a substrate, and has found that expression levels of the transcription factor or a substance which interacts with the factor can be profiled by the chip based on a biological function such as DNA binding capacity.

The present invention provides the following transcription chips and assay methods of the transcription factor by the use thereof.

[1] A transcription chip wherein at least one polynucleotide comprising one or more element sequences to which a transcription factor can be bound is immobilized on a substrate.

[2] The chip according to [1] wherein at least two polynucleotides comprising one or more element sequences to which transcription factors can be bound respectively are bound.

[3] The chip according to [1] wherein the above polynucleotide has a partial sequence of a promoter in the upstream (5') side of each gene.

[4] The chip according to [1] wherein the above substrate is made by forming a diamond thin film on a support.

[5] The chip according to [1] wherein the above polynucleotide is bound to the diamond thin film through a optionally appropriate spacer.

[6] A method for assaying a binding of a transcription factor comprising a step of interacting a sample capable of comprising the transcription factor with the transcription chip according to any of [1] to [5].

[7] The method according to [6] for evaluating an effect of a subject substance on a transcription factor, wherein the above sample is a cell lysate of cells cultured in the presence of the subject substance.

[8] The method according to [6] or [7] wherein the binding of the transcription factor is detected using an antibody against the transcription factor or a method utilizing mass spectrometry.

[9] The method according to [8] wherein the detection using the antibody is an ELISA and the method utilizing the mass spectrometry is a peptide mass fingerprint method.

BRIEF DESCRIPTION OF DRAWINGS

FIG. 15 shows results of database search by PMF.

FIG. 22 shows results of identified NFκB obtained by MASCOT database search.

The present invention will be described in more detail below.

Figure 1:
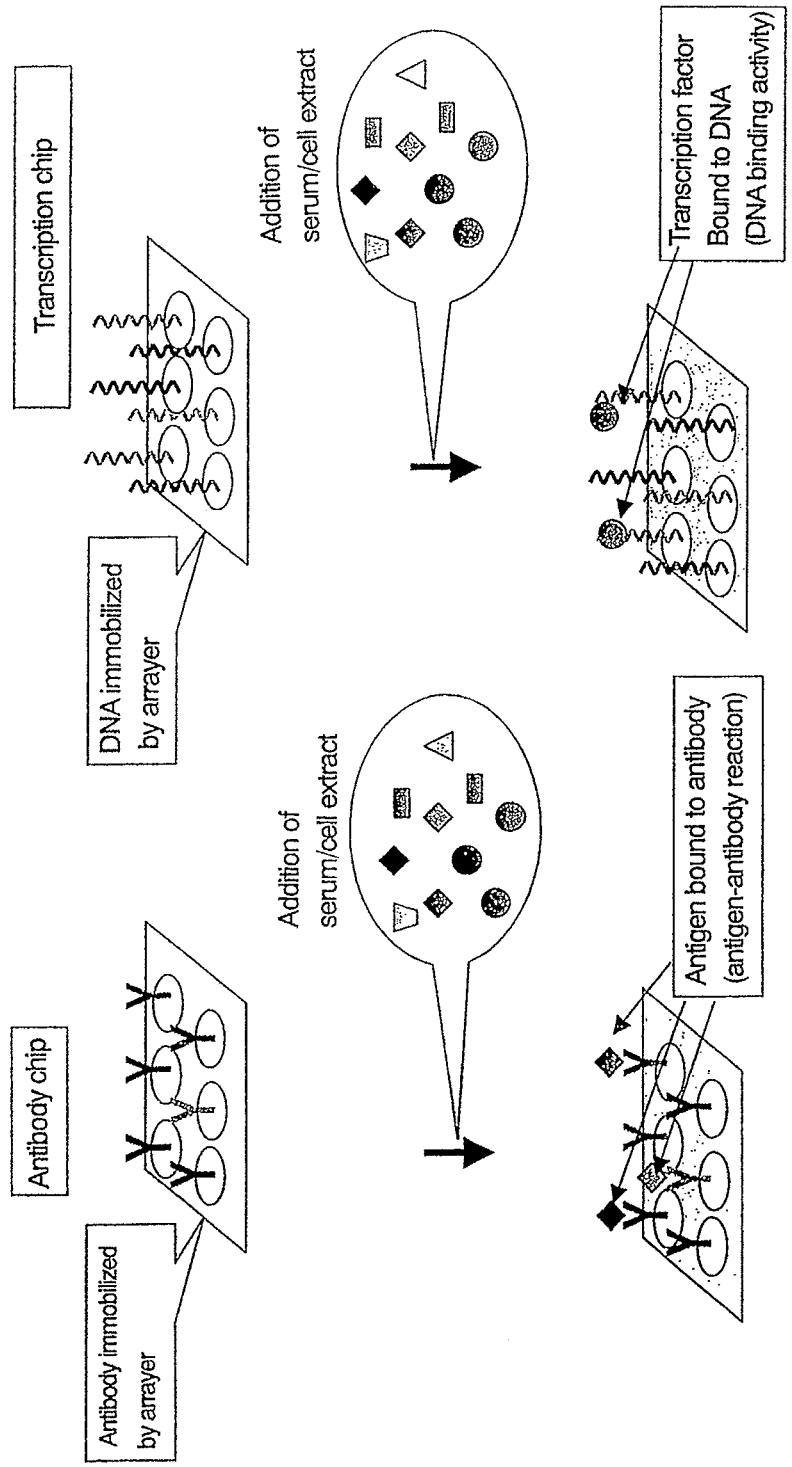
FIG. 1 shows an antibody chip and a transcription chip in comparison.

The transcription chip of the present invention is different from both the antibody chip and the DNA chip (FIG. 1). The transcription factor is deeply involved in cellular inflammatory response, carcinogenesis and transcription controlling factor activation because it is the protein which is bound to a region called an element sequence in an upstream region of each gene and regulates the expression of various genes. Therefore, it is very important to, at a protein level, profile various transcription factors which keep biological activity.

The transcription factor is a factor which is bound to a DNA and is involved in transcription regulation such as transcription initiation. For example, NFκB (e.g., p50, p65), NFATc1, CREB, ATF-2, c-Jun, c-Rel, c-Fos, AP1, AP-2, RBP-J, Nrf2, KLF5, BTEB2, NF-AT, MITF, RUNX family, GATA-1, GATA-2, HIF1α, HLF, Brn-3, EBP, CDP, c-Myb, c-Myc, E2F, EGR, Ets, Ets1/PEA3, FAST-1, BRCA1, HNF-4, GATA, NF-1, Max, IRF-1, NFATc, NF-E1, NF-E2, 1-Oct, MEF-1, MEF-2, Myc-Max, p53, Pax-5, Pbx1, TR, AhR, ER, GR, MR, AR, VDR, RAR, RXR, LXR, FXR, PPAR, ERR, ROR, SXR, PXR, USF-1, Sp1, Stat1, Stat3, Stat4, Stat5, Stat6, COUP-TF, Ftz-F1, TFIIB, TFIID, TBP, TFIIE, TFIIF, TFIIH, TAF, PolI, PolII, PolIII, ELL, TFIIS, Elongin, P-TEFb, DSIF, CBP/p300, p160 (SRC-1, TIF2, AIB1) TRRAP/GCN5, NcoR, SMRT, HDAC, DRIP/TRAP, Smad, and the like are exemplified.

As the transcription factor, the mammalian transcription factor is preferable, and in particular, the human transcription factor is preferable.

The element sequences are publicly known, and a polynucleotide comprising one or two or more of various element sequences can be appropriately formed on the chip. Specific element sequences include sequences (GGAATTTCCC (SEQ ID NO. 23) and GGGAAATTCC (SEQ ID NO: 24); GGGGATCCCC and GGGATCCCC; TGACTCAT and ATGAGTCA; AGGTCA and TGACCT; AGGTCA and TGACCT; AGGTCA and TGACCT; AGGTCATGACCT (SEQ ID NO: 25); AGAACA and TGTTCT; TGACGTCA) underlined in primers in the following Example 1. Other element sequences are described in for example, Sagroves et al.'s report (Cancer Cell 1:211-212 (2002) and Ishii et al.'s report (Science 232:1410-1413 (1986)).

As the element sequence, the element sequence to which the mammalian transcription factor can be bound is preferable, and in particular, the element sequence to which the human transcription factor can be bound is preferable.

It is preferable that oligonucleotides corresponding to multiple transcription factors whose dynamics is required to be figured out are immobilized on the chip of the present invention because all of the transcription factors can be profiled on one chip. Of course, the oligonucleotide corresponding to only one transcription factor may be immobilized on one array, and the transcription factors may be profiled using a required number of the chips.

At least one element sequence can be contained in one polynucleotide, one or more of the same element sequences may be contained, and two or more element sequences may be contained in one polynucleotide.

The polynucleotide comprising the element sequence, which is bound onto the substrate may be artificially made by binding appropriate oligonucleotides or polynucleotides to each end of the element sequence known publicly, but it is possible to preferably use a partial sequence of a promoter in the upstream (5') side of each gene. A length of the polynucleotide is not particularly limited, but, for example, is the length composed of about 10 to 500, preferably about 15 to 300, and more preferably about 20 to 100 nucleotides.

The polynucleotide composed of excessively long base pairs is difficult to be prepared, produces self-complementary base pairs, is hybridized at a different site from the target site, and thus no objective oligonucleotide is likely to be obtained.

As the polypeptide comprising the element sequence, the polynucleotides in SEQ ID NOS:1 to 22 are exemplified.

The substrate is not particularly limited as long as it can bind the DNA, and it is possible to use those in which carboxyl group is introduced by binding an aqueous polymer such as carboxymethyl dextran and PEG modified terminally with the carboxyl group to the substrate surface, but preferably, the chips having diamond thin film where numerous carboxyl residues are formed on the surface, e.g., GeneDia™ (registered trade mark), DLC chip are exemplified. The substrate having the diamond thin film is preferable, and in particular GeneDia™ is preferable because numerous double-stranded DNA can be bound thereto at high density. The diamond thin film can be formed on any of supports, e.g., a silicon substrate.

Figure 20:
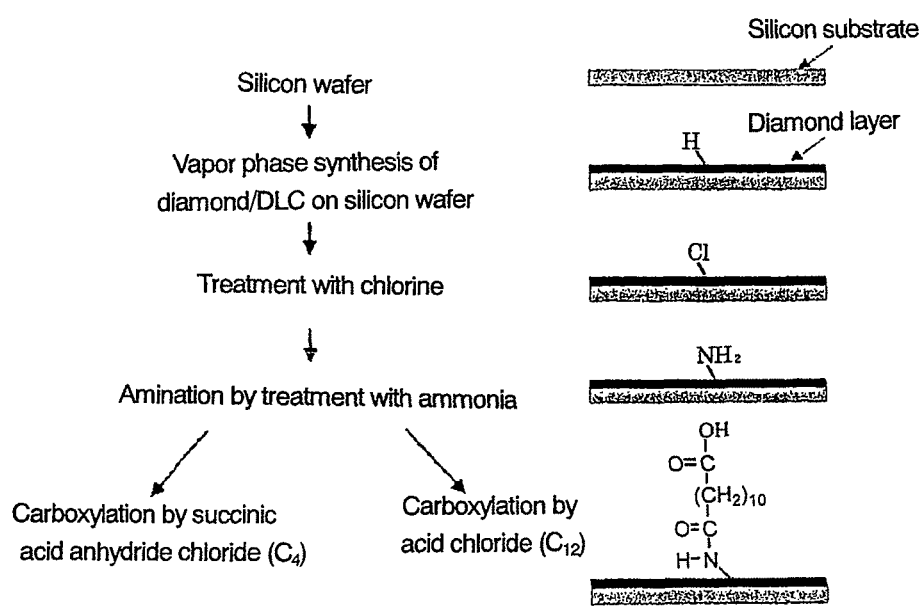
FIG. 20 shows a method for modifying a substrate having a diamond thin film.

An outline of a method for introducing a substituent such as amino group and carboxyl group onto the diamond thin film is shown in FIG. 20.

The binding of the DNA and the substrate can be performed by a coupling reagent. The coupling reagent includes reagents used for forming ordinary peptide bonds, and for example, carbodiimides (DCC, WSC) and carbonyldiimidazole and the like are exemplified. Alternatively, COOH terminal group on the substrate can be made into active ester such as N-hydroxysuccinic acid imide and 1-hydroxybenzotriazole using the above carbodiimides, particularly water-soluble carbodiimide, and bound to the DNA having a binding group such as amino group at the 5' or 3' terminus. Furthermore, the distance between the substrate and the DNA may be appropriately extended by binding the DNA through an appropriate spacer, and a binding sequence of the transcription factor may be estranged from the substrate of the transcription chip by placing an appropriate sequence (e.g., sequence derived from the promoter) between the binding site of the DNA and the binding site of the transcription factor. By the use of the appropriate promoter, it becomes possible to immobilize the binding sequence for the transcription factor with keeping a certain space from the surface, and the assay of the transcription factor can be performed with assuring mobility of the transcription factor.

In Examples of the present invention, the polynucleotide having $NH_2(CH_2)_{12}$ at the 5' terminus was used. Such a modified oligonucleotide comprising the substituent (e.g., $NH_2(CH_2)_{12}$) having the binding group such as amino group at the 5' or 3' terminus can be produced in accordance with publicly known methods, e.g., the methods disclosed below and in JP HEI-3-74239 B.

The chip of the present invention is used for detecting a transcription factor by binding double-stranded DNA on the substrate, binding the transcription factor to an element sequence of the double-stranded DNA and detecting the bound transcription factor using mass spectrometry or an antibody in accordance with an appropriate detection method.

The double-stranded DNA may be bound by binding single strand DNA (binding the polynucleotide through this onto the substrate) having a reactive group such as amino group at the 5' or 3' terminus onto the substrate and subsequently hybridizing the polynucleotide complementary thereto, or by directly binding the double-stranded DNA having at least one chain binding group (e.g., $NH_2$) onto the substrate.

The transcription chip made in this way is then contacted with a sample which can comprise a transcription factor to bind the transcription factor onto the chip. As such a sample, cell lysate of mammalian cells is preferable, and in particular the cell lysate of human cells is preferable. For example, effect of various culture conditions and subject substances on the transcription factor can be quantitatively evaluated by profiling transcription factors in cell lysate from various human cell lines cultured under various culture conditions or in the presence of the subject substance using the chip of the present invention.

The transcription factor can be quantified by immunologically measuring using an antibody against the transcription factor and a publicly known method such as ELISA or measuring using mass spectrometer. For example, the transcription factor may be directly measured by mass spectrometer, but it is preferable to identify and quantify the bound transcription factor by digesting the transcription factor bound to the chip with an appropriate protease such as trypsin, analyzing the resulting peptide fragments by mass spectrometer and comparing with a mass spectrum pattern (mass fingerprint) of the protease-digested transcription factor. As the mass spectrometer, MALDI-TOF is preferably exemplified.

In ELISA, various blocking agents such as tris-, skim milk-, gelatin- and ethanolamine-based blocking agents can be used to enhance the specificity.

It is preferable to label the oligonucleotide of the invention with a fluorescent dye such as fluorescein such as FITC, rhodamine, cy2, cy3 and cy5 or a luminescent substance such as acridium ester, luminol and luminescent adamantane.

BEST MODES FOR CARRYING OUT THE INVENTION

The present invention will be described in more detail with reference to the following Examples.

Example 1

(1) Experimental Materials and Methods
(i) Experimental Apparatuses

Fluorescent scanner: CRBIO II (Hitachi Software Engineering Co., Ltd.), microarrayer: SPBIO (Hitachi Software Engineering Co., Ltd.), microplate reader: µ Quant (BIO-TEK), plate shaker: Micro mixer MX-4 (Sanko Junyaku Co., Ltd.), $CO_2$ incubator: HERAcell (Kendro), mass spectrometer: ABI4700 Proteomics Analyzer (Applied Biosystems), and Voyager-DESTR (Applied Biosystems).

(ii) Experimental Materials

Chips, plates: DLC chips (3 mm, 3 mm) (Toyo Kohan Co., Ltd.), GeneDia™ C4 (3 mm, 3 mm) (Toyo Kohan Co., Ltd.), 96-well U-bottom microplate (Greiner), NFκB (p50) (Promega), antibody: anti-NFκB p50 antibody (Active Motif), anti-NFκB p50 antibody (Rockland, #100-4164), POD-labeled anti-rabbit IgG (Active Motif), AP-labeled anti-rabbit IgG (Nacalai Tesque Inc.), FITC-labeled anti-rabbit IgG (Nacalai Tesque Inc.), BD Mercury TransFactor kit Inflammation 1 (BD Biosciences).

Reagents: WSC (Dojin), NHS (Wako), POD color development substrate TMBZ (Sumitomo Bakelite Co., Ltd., #ML-1120T), activation buffer 1 (10 mM WSC, 0.1 M MES, pH 4.5), activation buffer 2 (100 mM WSC, 20 mM NHS, 0.1 M NaPB, pH 6.0), blocking buffer (1 M Tris-HCl (pH 8.0), 150 mM KCl, 0.1% Tween 20), binding buffer (1% BSA, 10 mM HEPES buffer, pH 7.5, 10 µg/ml salmon sperm DNA, 2 mM DTT, diluted (×100) protease inhibitor cocktail (SIGMA)), washing buffer (50 mM NaCl, 10 mM NaPB (pH 7.5), 0.1% Tween 20), Protein Assay Reagent (BioRad), TNFα (Wako #203-15263), phorbol 12-myristate 13-acetate (PMS) (SIGMA #P1585), sinapic acid solution (1 mg/mL sinapic acid, 50% acetonitrile, 0.1% Trifluoroacetic acid (TFA)), α-Cyano-4-hydroxycinnamic acid (α-CHCA) solution (1 mg/mL α-CHCA, 50% acetonitrile, 0.1% TFA), low salt concentration buffer (5 mM Tris-HCl (pH 8.0), 1 mM NaCl), trypsin reaction solution (50 mM ammonium bicarbonate, 0.1-4 µg/mL trypsin), GFX purification kit (Amersham, #27-9602-01), NE-PER Nuclear and Cytoplasmic extraction reagents (PIERCE #78833) ProteoMass™ Peptide MALDI-MS calibration kit.

Oligonucleotides: The following primers and oligonucleotides were synthesized. Underlines indicate recognition sequences (element sequences) of transcription factors. The oligonucleotide was mixed with a complementary chain thereof so that a final concentration of double-stranded DNA was 50 µM, treated with heat at 95° C. for 5 min, and gradually cooled.

```
(PCR primers)
                                                                      (SEQ ID NO: 1)
PRD F primer  5'-NH2(CH2)12-CCTCACAGTTTGTAAATCTTTTTCCC-3'

(SEQ ID NO: 2)
PRD R I primer  5'-FITC-GGCCTATTTATATGAGATGGTCCTC-3'

(SEQ ID NO: 3)
PRD R II primer  5'-FITC-AGAGGAATTTCCCACTTTCACTTC-3
(Immobilized oligonucleotides)

PRD II:
                                                                      (SEQ ID NO: 4)
5'-NH2(CH2)12-GGGAGCTGAGTAGGGAAATTCCATGCATGCGGGAAATTCCCATG-3'

(SEQ ID NO: 5)
5'-CATGGGAATTTCCCGCATGCATGGAATTTCCCTACTCAGCTCCC-3'
```

-continued (SEQ ID NO: 6)
5'-FITC-CATGGGAATTTCCCGCATGCATGGAATTTCCCTACTCAGCTCCC-3'

IgκB:
(SEQ ID NO: 7)
5'-NH$_2$(CH$_2$)$_{12}$-GGGAGCTGAGTAGGGGATCCCATGCATGCGGGGATCCCCATG-3'

(SEQ ID NO: 8)
5'-FITC-CATGGGGATCCCCGCATGCATGGGATCCCCTACTCAGCTCCC-3'

AP1:
(SEQ ID NO: 9)
5'-NH$_2$(CH$_2$)$_{12}$-GGGAGCTGAGTATGACTCATATGCATGCTGACTCATCATG-3'

(SEQ ID NO: 10)
5'-CATGATGAGTCAGCATGCATATGAGTCATACTCAGCTCCC-3'

VDRE:
(SEQ ID NO: 11)
5'-NH$_2$(CH$_2$)$_{12}$-GGGAGCTGAGTAAGGTCAAGGAGGTCAATGCATGCAGGTCAAGGAGGTCACATG-3'

(SEQ ID NO: 12)
5'-CATGTGACCTCCTTGACCTGCATGCATTGACCTCCTTGACCTTACTCAGCTCCC-3'

RARE:
(SEQ ID NO: 13)
5'-NH$_2$(CH$_2$)$_{12}$-
GGGAGCTGAGTAAGGTCACCAGGAGGTCAATGCATGCAGGTCACCAGGAGGTCACATG-3'

(SEQ ID NO: 14)
5'-CATGTGACCTCCTGGTGACCTGCATGCATTGACCTCCTGGTGACCTTACTCAGCTCCC-3'

ERE:
(SEQ ID NO: 15)
5'-NH$_2$(CH$_2$)$_{12}$-GGGAGCTGAGTAAGGTCACAGTGACCTATGCATGCAGGTCACAGTGACCTCATG-3'

(SEQ ID NO: 16)
5'-TCAGGTCACAGTGACCTGATCTCAGGTCACAGTGACCTTTCACGAGGTAC-3'

TRE:
(SEQ ID NO: 17)
5'-NH$_2$(CH$_2$)$_{12}$-GGGAGCTGAGTAAGGTCATGACCTATGCATGCAGGTCATGACCTCATG-3'

(SEQ ID NO: 18)
5'-CATGAGGTCATGACCTGCATGCATAGGTCATGACCTTACTCAGCTCCC-3'

GRE:
(SEQ ID NO: 19)
5'-NH$_2$(CH$_2$)$_{12}$-GGGAGCTGAGTAAGAACACTGTGTTCTATGCATGCAGAACACTGTGTTCTCATG-3'

(SEQ ID NO: 20)
5'-CATGAGAACAGACTGTTCTGCATGCATAGAACAGACTGTTCTTACTCAGCTCCC-3'

CRE:
(SEQ ID NO: 21)
5'-NH$_2$(CH$_2$)$_{12}$-GGGAGCTGAGTATGACGTCAATGCATGCTGACGTCACATG-3'

(SEQ ID NO: 22)
5'-CATGTGACGTCAGCATGCATTGACGTCATACTCAGCTCCC-3'

(iii) Experimental Methods
i. Preparation of Chips for Immobilization of Element Sequences (for ELISA)

Chips (DLC or GeneDia™) were set with coating side up in a 96-well U-bottom microplate made from polypropylene. Subsequently, 50 µL of the activation buffer 1 comprising double-stranded DNA element sequences at various concentration was added, and the plate was sealed. Then, the plate was shaken on a plate shaker at room temperature for one hour. The plate was washed twice with the washing buffer. Then, 200 µL of the blocking buffer was added, the plate was shaken at room temperature for one hour, and subsequently stored at 4° C.

ii. On-Chip Enzyme-Linked Immunosorbent Assay (on Chip ELISA)

The plate was washed twice with the washing buffer, NFκB at various concentrations diluted with the binding buffer was added, and the plate was shaken at room temperature for one hour. The plate was washed three times with the washing buffer, anti-NFκB antibody diluted 2000 times with antibody diluting buffer was added, and the plate was shaken at room temperature for one hour. The plate was washed three times with the washing buffer, POD-labeled anti-rabbit IgG secondary antibody diluted 2000 times with the antibody diluting buffer was added, and the plate was shaken at room temperature for one hour. The plate was washed five times with the washing buffer, and subsequently absorbance at a wavelength of 450 nm based on the absorbance of TMBZ which was a color development substrate of POD was measured by a microplate reader.

iii. Preparation of HeLa Cell Extract

HeLa cells was cultured up to 70% confluence in 25 mL of DMEM medium to which 10% Fetal Bovine Serum (FBS)

had been added using 250 cm² dish in a CO$_2$ incubator at 37° C. After changing the medium to serum free medium, TNFα was added at a final concentration of 100 ng/mL, and then the cells were cultured in the CO$_2$ incubator at 37° C. for 30 minutes. The cells detached with a cell scraper were centrifuged (×1000 g, 5 minutes) to remove the medium. FBS was added and mixed, and then the mixture was centrifuged (×1000 g, 5 minutes) again to remove a supernatant. The cell lysis buffer was added to a cell pellet to lyse the cells. A cell lysate was centrifuged (×1000 g, 5 minutes), then the supernatant was collected, and a protein concentration therein was measured. The on-chip ELISA was performed using 60 μg of the protein derived from the cell lysate per chip. Meanwhile, for profiling the transcription factor, nuclear extracts derived from the HeLa cells stimulated with TNFα (100 ng/mL) or PMA (1 μg/mL), or unstimulated control were used. The nuclear extracts were prepared using a kit from Pearce. The on-chip ELISA was performed using 20 μg of the protein derived from the nuclear extract per chip.

iv. Preparation of Arrayed Double-Stranded DNA on Chip

DLC chips were set with coating side up in a 96-well U-bottom microplate made from polypropylene. Subsequently, 50 μL of the activation buffer 2 was added, and the plate was sealed and shaken on the plate shaker at room temperature for 30 minutes. The plate was washed twice with distilled water, and dried by centrifugation. The activated DLC chip was set in a microarrayer, and then 25 μM 30% double-stranded oligonucleotide prepared in glycerol was spotted on the activated DLC chip using a 150 μm pin. The chips were incubated at 50° C. for 12 hours, blocked using the blocking buffer, and then stored at 4° C.

v. Fluorescence Detection of Transcription Chip Array

After washing twice with the washing buffer, NFκB diluted at 100 ng/mL with the binding buffer was added, and shaken at room temperature for one hour. After washing three times with the washing buffer, anti-NFκB antibody (RCK) diluted 100 times with antibody diluting buffer was added, and shaken at room temperature for one hour. After washing twice with the washing buffer, FITC-labeled anti-rabbit IgG antibody diluted 50 times with the antibody diluting buffer was added, and shaken at room temperature for one hour. After washing twice with the washing buffer, at a fluorescence wavelength of 535 nm based on Fluorescence of FITC excited with laser at a wavelength of 473 nm, fluorescent intensity was detected by CRBIO II micro array scanner.

vi. Detection of Transcription Factor Captured onto Transcription Chip by MALDI-TOF MS Chips (DLC or GeneDia™) were set with coating side up in a 96-well U-bottom microplate made from polypropylene. Subsequently, 50 μL of the activation buffer 1 comprising double-stranded DNA element sequences at various concentrations was added, and the plate was sealed. Then, the plate was shaken on the plate shaker at room temperature for one hour. The plate was washed twice with the washing buffer. Then, 200 μL of the blocking buffer was added, the plate was shaken at room temperature for one hour, and subsequently stored at 4° C. After washing twice with the washing buffer, NFκB diluted with the binding buffer at various concentrations was added, and shaken at room temperature for one hour. After washing three times with the washing buffer, the plate was washed with the low salt concentration buffer. Subsequently, the chips were dried by centrifugation. The chip was fixed with a MALDI plate using two sided tape, then, 1 μL of 1 mg/mL sinapic acid solution was added as a matrix to the chip, and was dried.

vii. On-Chip Digestion and Peptide Mass Fingerprint

The chips were transferred to a new ELISA plate, 1 μL of a trypsin reaction solution was added to the chip surface, the chips were incubated at 37° C. for 2 to 6 hours, and the reaction was terminated by adding 1 μL of 0.1% TFA. Subsequently, 1 μL of 1 mg/mL α-CHCA solution was added as a matrix to the chip, and was dried. In that, 0.5 μL was spotted on an MALDI plate. A peptide map was analyzed using MS-Fit Search.

viii. Identification of Captured Molecule by Tandem Mass Spectrum

Using the aforementioned method, NFκB was captured onto DLC, and on-chip trypsin digestion was performed. A peptide mass fingerprint was acquired by ABI4700 proteomics analyzer using ProteoMass™ Peptide MALDI-MS Calibration kit for mass calibration. Obtained PMF of NFκB was used for tandem mass analysis.

Figure 2:
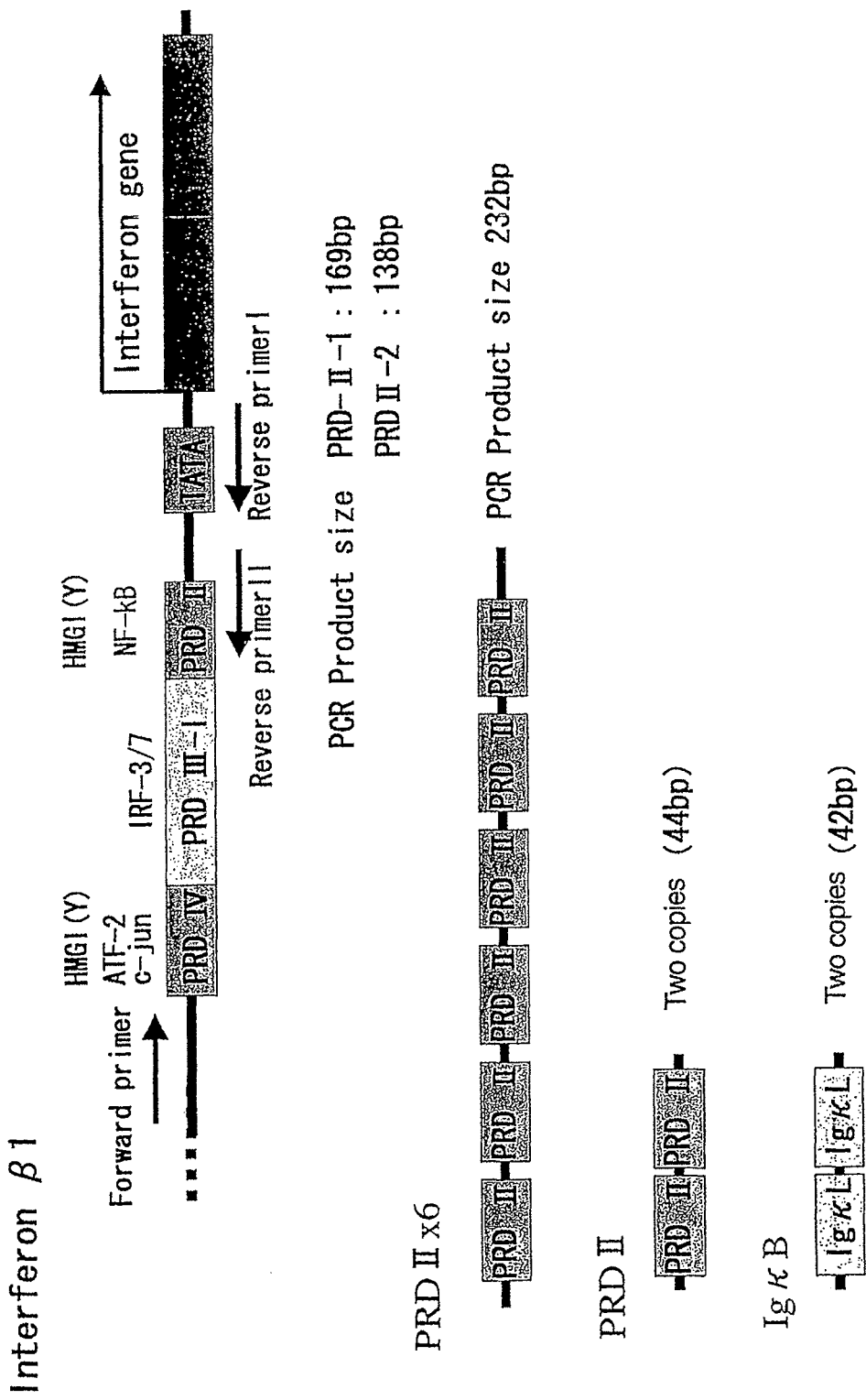
FIG. 2 shows immobilized genes.
Figure 3:
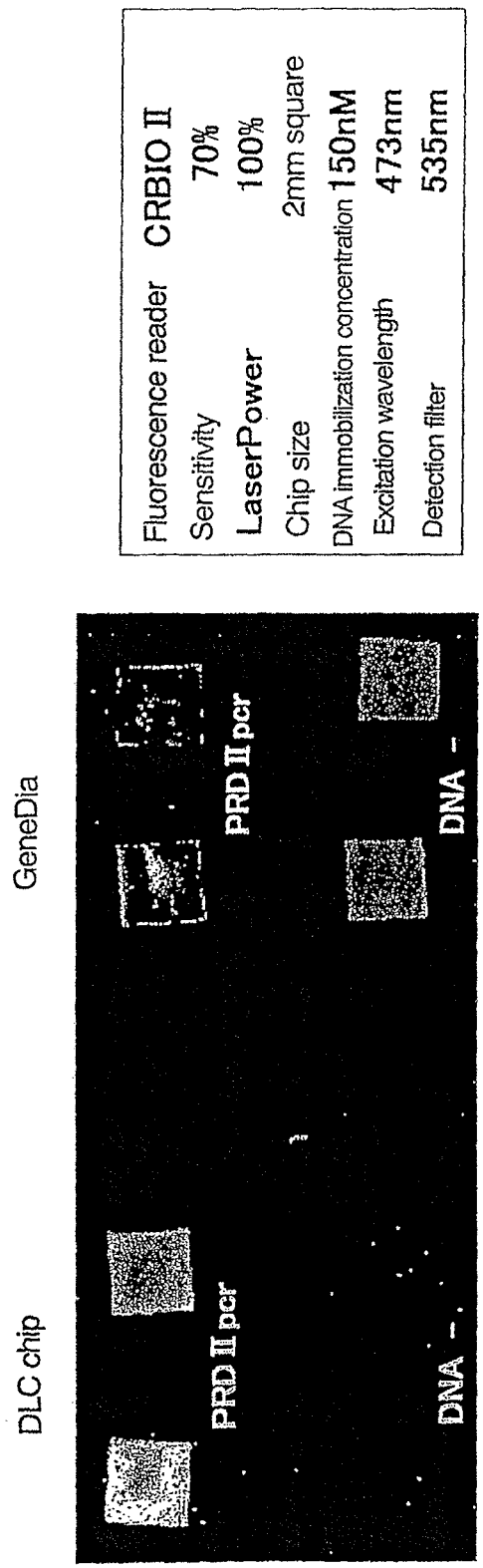
FIG. 3 shows chips to which FITC-labeled NFκB response sequence (PRDII-1) has been immobilized.

(3) Experiment Results (A) Investigation of Basic Conditions i. Immobilization of Double-Stranded DNA onto GeneDia™ and DLC Chips A fragment of the region including an element region present in an upstream sequence of interferon β1 gene among the element sequences which NFκB recognized was acquired by PCR method using PRD F primer and PRD RI primer (PRD II-1, FIG. 2). A PCR product was purified using GFX purification kit, and immobilized. Consequently, it was confirmed that double-stranded DNA was bound to both DLC and GeneDia™ chips (FIG. 3).

ii. Investigation of Optimal Condition for on-Chip ELISA (DLC)

a. Competitive Inhibition Experiment

Figure 4:
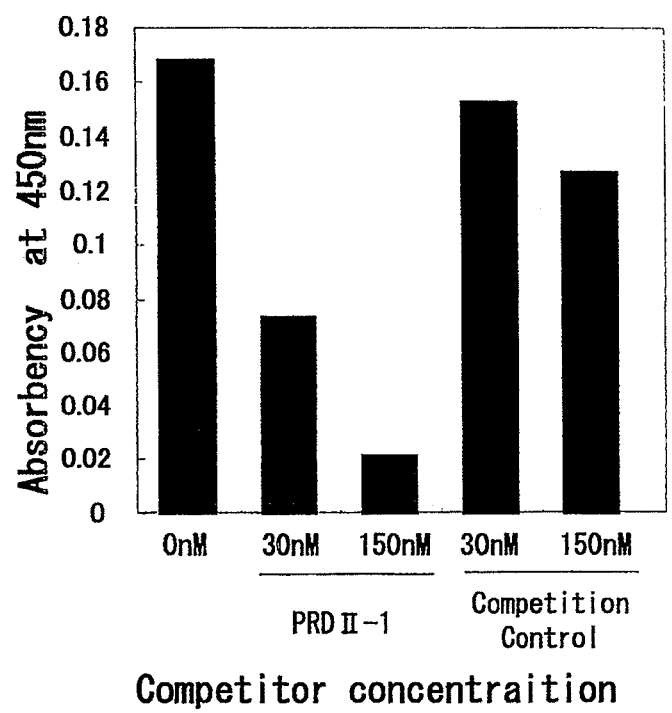
FIG. 4 shows a result of a competition experiment of the NFκB response sequence.

In order to investigate whether it is possible to capture the transcription factor by the double-stranded DNA immobilized on the chip and specifically detect it by ELISA, it was investigated whether PRD II-1 competes with the immobilized PRD II-1 for the binding NFκB by adding the PRD II-1 into the binding buffer. As a control, the experiment was performed by adding the double-stranded oligonucleotide which did not contain the immobilized PRD II-1 sequence into the binding buffer. As a result, the capture of NFκB onto the chip was strongly inhibited in a concentration dependent manner when the PRD II-1 had been added into the binding buffer whereas almost no inhibitory effect was observed when the control sequence was used (FIG. 4). From the above, it has been suggested that NFκB specifically recognizes and binds the PRD II-1 sequence on the DLC chip.

b. Investigation of Immobilized DNA Sequence

Figure 5:
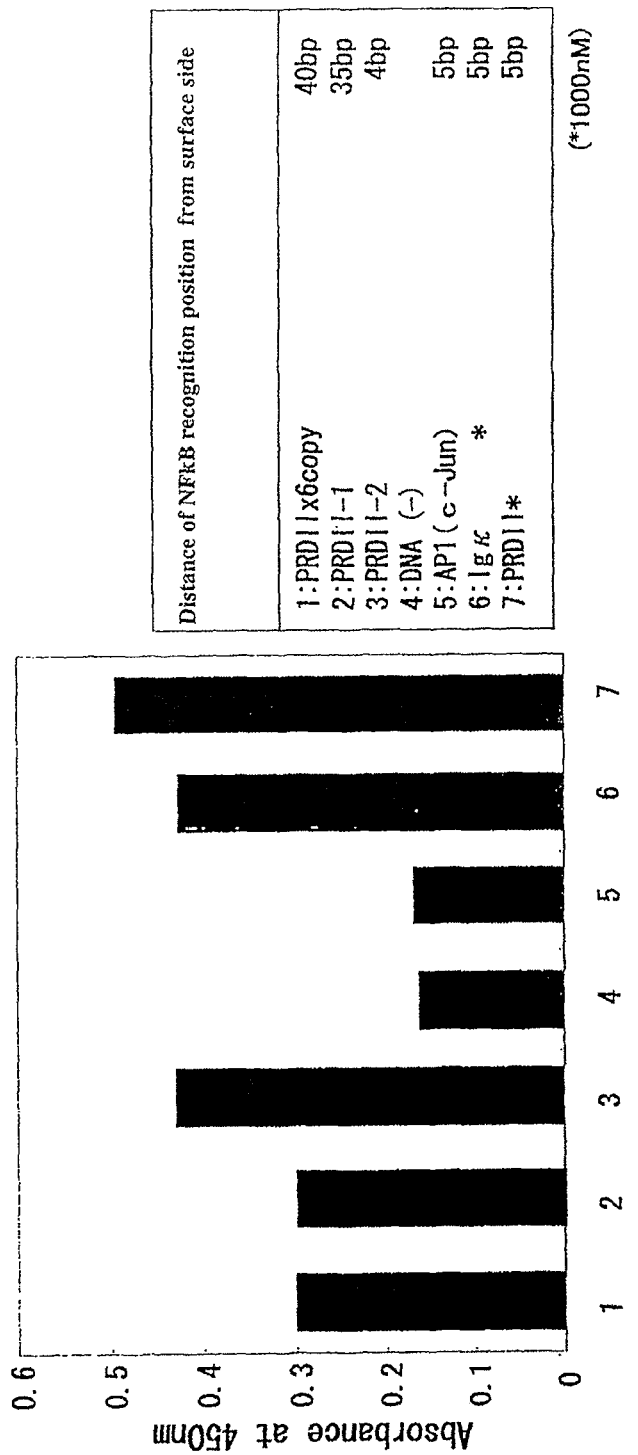
FIG. 5 shows a result of examining immobilized double-stranded DNA.

In order to investigate an ELISA condition for NFκB, the double-stranded DNA comprising the element DNA sequence different in length and copy number were synthesized by the PCR method or a synthetic method, and analyzed. When PRD II-1 comprising one copy of the PRD II sequence was compared with PRD II-2, the immobilized PRD II-2 was more excellent in efficiency of trapping NFκB (FIG. 5). Even when PRD II-2 was compared with the PCR product (PRD II×6) comprising 6 copies of the same element sequence, the immobilized PRD II-2 was more excellent in immobilization efficiency. Next, without using the PCR method, it was investigated whether NFκB could be efficiently captured using the oligonucleotide artificially synthesized. When using the double-stranded oligonucleotide comprising two copies of NFκB-binding element sequence IgκB derived from immunoglobulin and the oligonucleotide PRD II comprising two copies of the PRD II sequence, the trapping efficiency of NFκB equivalent to or more than that of PRD II-2 was observed (FIG. 5).

From the above results, it has been suggested that it is possible to efficiently trap NFκB by the recognition sequence close to the NFκB recognition sequence at a peripheral end side (liquid phase side opposite to an immobilized site) of the PCR product or the double-stranded oligonucleotide, an NFκB-antibody complex is unlikely to access to the internal recognition sequence due to steric hindrance, and the copy number is not important for trapping NFκB in the ELISA detection system. However, it has been revealed that it is necessary to investigate the blocking condition to enhance the specificity because in the negative control where an AP1 sequence was immobilized or no DNA was immobilized, about 30 to 50% color development was observed.

c. Investigation of Blocking Condition

Figure 6:
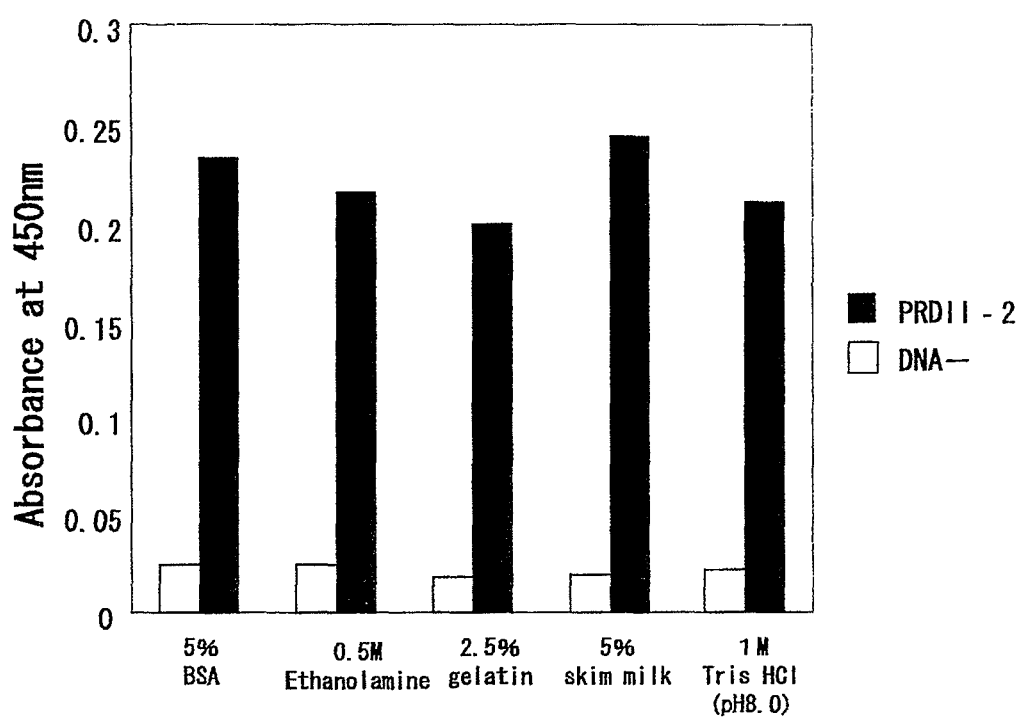
FIG. 6 shows a result of examining blocking agents.

In order to enhance the specificity of the ELISA, various blocking agents were examined. As blocking buffers, tris-based (1 M Tris-HCl (pH 8.0), 150 mM KCl, 0.1% Tween 20), skim milk-based (5% skim milk, 150 mM KCl, 0.1% Tween 20), BSA-based (5% BSA, 150 mM KCl, 0.1% Tween 20), gelatin-based (2.5% gelatin, 150 mM KCl, 0.1% Tween 20), and ethanolamine-based (150 mM ethanolamine, 150 mM KCl, 0.1% Tween 20) buffers were used. As a result, no large difference in specificity was observed among them (FIG. 6). Thereafter, tris-based buffer was used as the non-protein blocking agent. Reproducibility among measurements could be enhanced by adding a step at 4° C., O/N subsequent to a blocking reaction time period at room temperature for one hour.

iii. Investigation of Reproducibility

Figure 7:
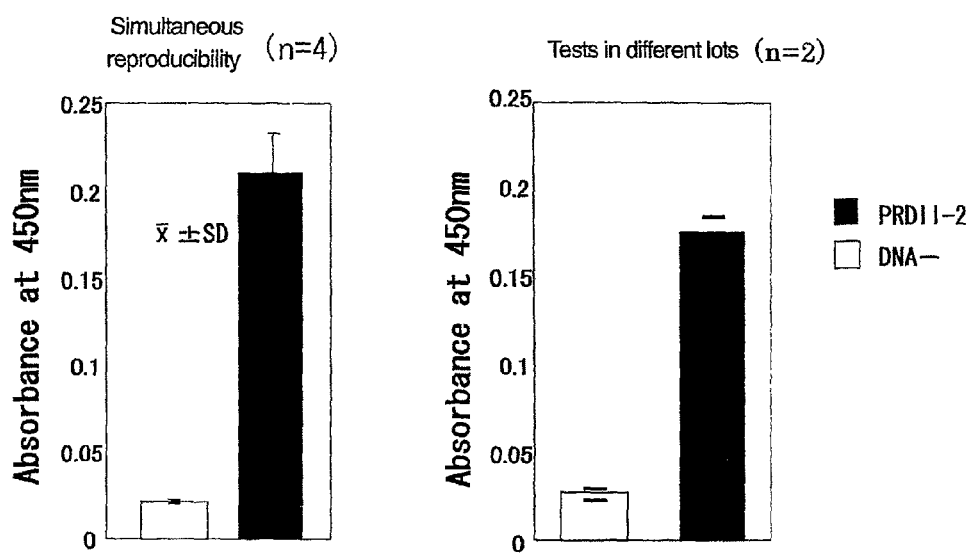
FIG. 7 shows results of a simultaneous reproducibility test and a reproducibility test between measurements (different lot competition: DLC).
Figure 8:
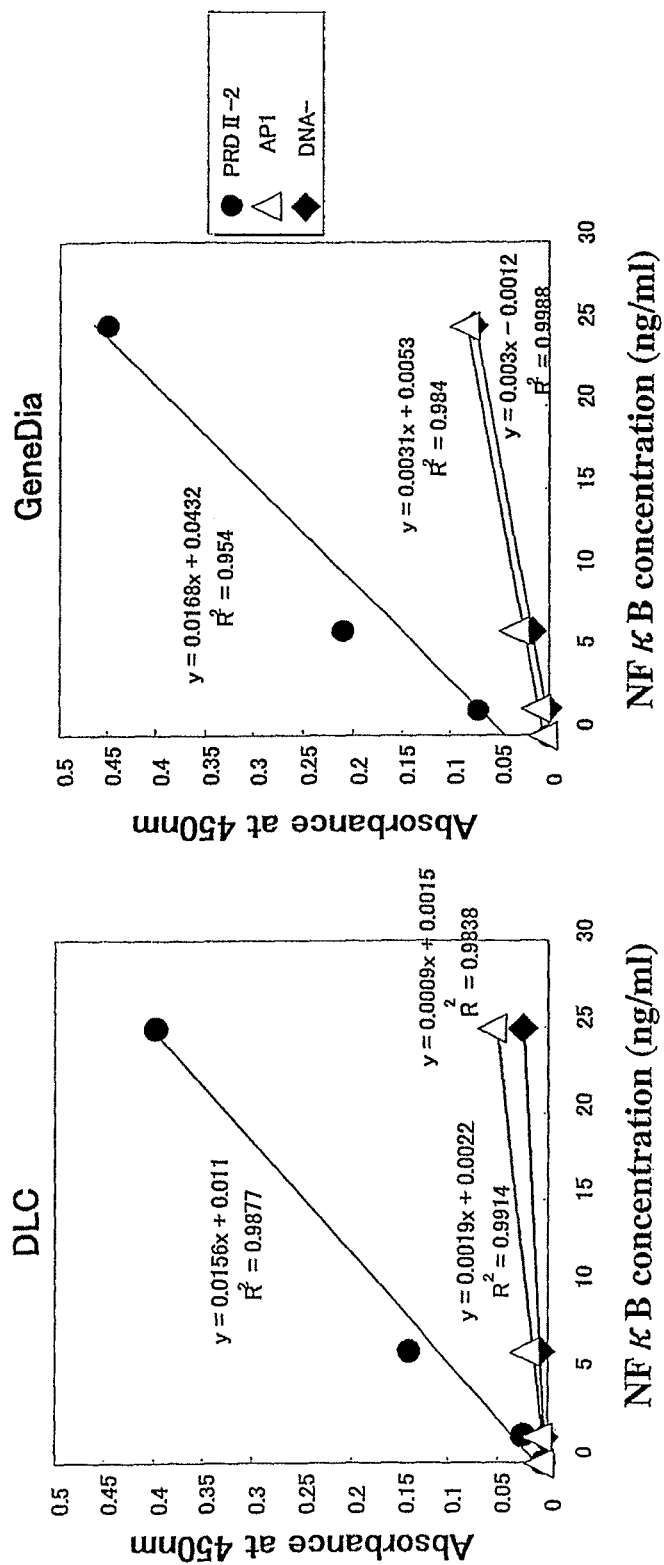
FIG. 8 shows comparison of GeneDia™ with DLC chip.
Figure 9:
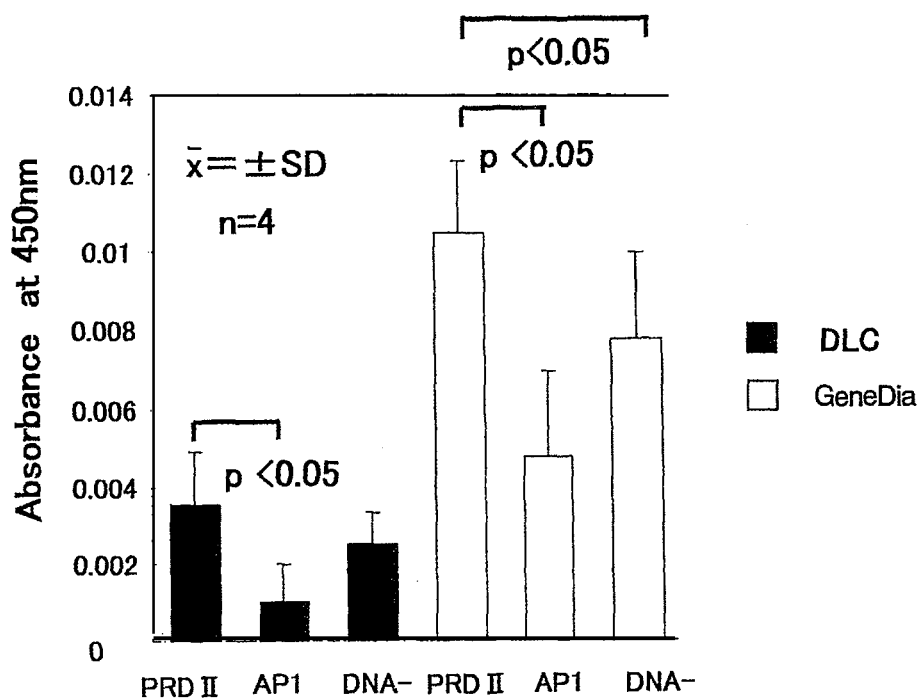
FIG. 9 shows a result of sensitivity test at a significant level of 5%.

Using the condition optimized in the previous section, simultaneous reproducibility and the reproducibility among the measurements of the DLC chips were examined. As a result, favorable results were obtained in the simultaneous reproducibility and the reproducibility among the measurements (FIG. 7).

iv. Comparison of GeneDia™ (Diamond Chip) and DLC Chip a. Comparison of Quantitativity by Concentration Change In order to compare the performances of DLC chip and GeneDia™, the comparison was performed under the same condition using NFκB at various concentrations. As a result, they exhibited the nearly same quantitativity, but at a lower concentration, GeneDia™ was more excellent in NFκB detection (FIG. 8).

b. Comparison of Detection Limit

In order to analyze the profiles at the low concentration range (10 ng/mL or less) in detail, the detection limit in each chip was attempted to be calculated. As a result, for Gene-Dia™, the PRD II-immobilized chip exhibited significant difference from the AP1 sequence-immobilized chip and the no DNA-immobilized chip at a significant level of 5% at both concentrations of 1.0 ng/mL and 0.33 ng/mL, whereas for DLC, the PRD II-immobilized chip exhibited the significant difference from both the AP1 sequence-immobilized chip and the no DNA-immobilized chip only at a concentration of 1.0 ng/mL (20 μM) (FIG. 2.1. 3-9). When using AP1 as a control, it was revealed that the detection limit was 0.33 ng/mL (6.7 μM) or less because the significant difference was observed only for the AP1-immobilized chip at a concentration of 0.33 ng/mL. Therefore, it has been suggested that it is possible to detect NFκB in the sample at a low concentration such as pM order. From these, it seems that it is also possible to construct the similarly highly sensitive on-chip ELISA system for the other transcription factor.

Figure 10A:
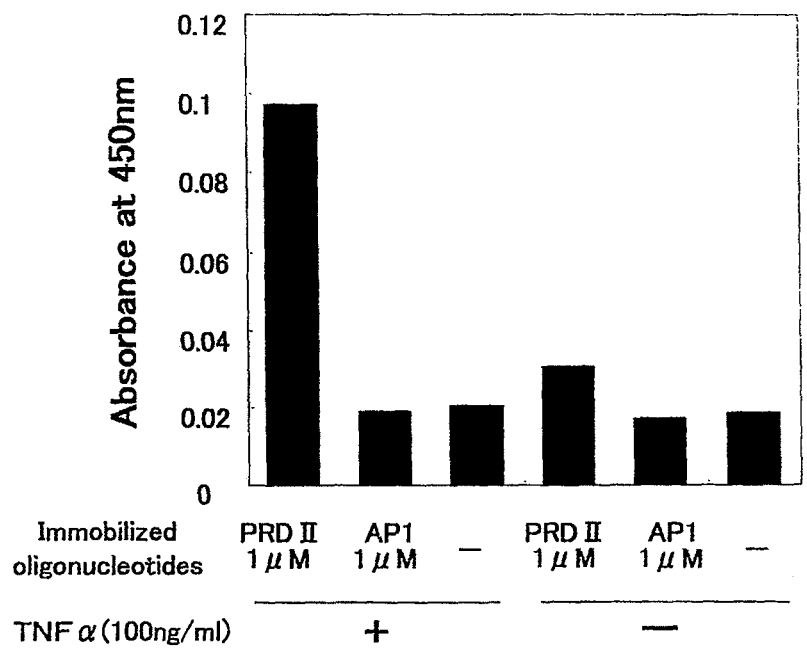
FIG. 10 shows results of NFκB detection in HeLa cell extracts (A), and expression profiling of inflammatory-related transcription factors in HeLa cells using GeneDia™ (B).

(B) Practical Application of Transcription Chips i. Detection of Transcription Factor in Culture Liquid The on-chip ELISA was performed to examine whether the transcription factor NFκB p50 can be captured from an extract of cultured HeLa cells. As a result, when using the extract of the cells stimulated with TNFα (100 ng/mL), stronger color development on the PRD II-immobilized chip was observed compared to the case of using the extract of unstimulated control cells (FIG. 10A).

Figure 10B:
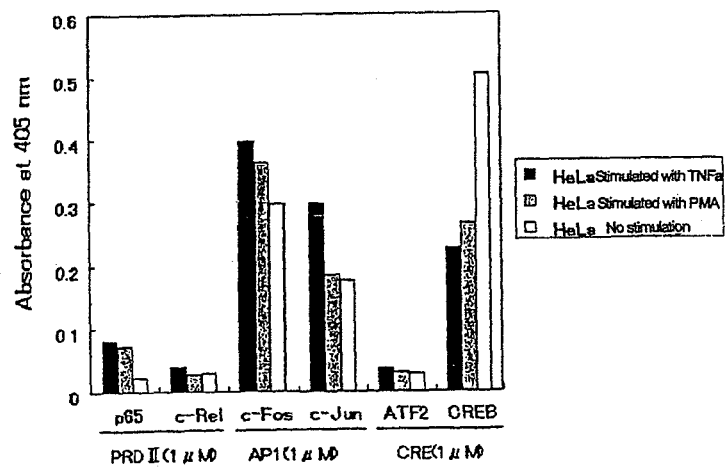

For the other transcription factors, it was examined whether the expression levels of various transcription factors were changed by the stimulation with TNFα or PMA (10 nM). In this method, an AP-labeled secondary antibody was used. As a result, many transcription factors (NFκB p65, c-Rel, c-Fos, c-Jun, ATF2, CREB) in addition to NFκB p50 could be specifically captured (FIG. 10B).

ii. Microarrayed Transcription Chip

Until now, it has been attempted that the double-stranded DNA chains are immobilized on a solid phase to capture a DNA-binding protein, which is then detected using the ELISA method. However, problems as the technology for proteome analysis have not been solved because throughput property and the number of samples simultaneously detected in multiple parameters are limited. In this section, the development of transcription microarray chips using the DLC chips as the technology in place of these methods will be reported.

a. Investigation of Making Arrayed Double-Stranded DNA

Figure 11:
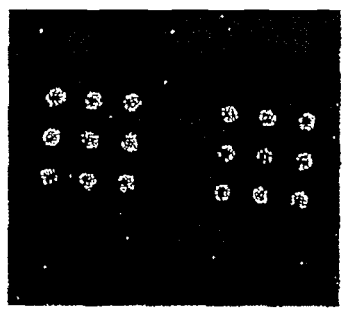
FIG. 11 shows microarrayed double-stranded DNA.

The DLC chip on which the FITC-labeled PRD II oligonucleotide had been immobilized at 9 spots was detected using CRBIO II fluorescence scanner (FIG. 11). It was revealed that the double-stranded DNA could be also immobilized similarly by spotting using an arrayer.

b. Specific Detection of NFκB from Transcription Microarray Chip

Figure 12:
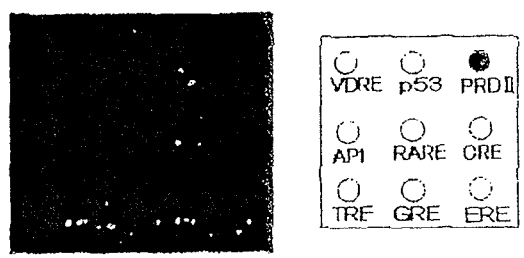
FIG. 12 shows a result of specific detection of NFκB by a fluorescent scanner.

The oligonucleotides comprising 9 element sequences, PRD II, AP1, p53, VDRE, RARE, CRE, TRE, GRE and ERE which were not labeled with FITC were similarly immobilized on the DLC chip. NFκB (100 ng/mL) was added to the DLC chip on which these 9 transcription factors had been arrayed, and detected by fluorescence immunoassay. As a result, the fluorescence was detected only from the oligonucleotide comprising PRD II which was the NFκB recognition sequence. From the above, it has been revealed that NFκB can be specifically detected on the DLC chip on which the element sequence has been arrayed (FIG. 12). Therefore, it is possible to construct the system in which multiple transcription factors are simultaneously detected in a sample in a small amount by combining antibodies which specifically recognize the transcription factors which is bound to the other element sequences.

iii. Detection of Transcription Factor by MALDI-TOF MS

The method of detecting the transcription factors by the on-chip ELISA is excellent in throughput as the system in which multiple transcription factors are simultaneously analyzed using specific antibodies, compared with the ELISA and the gel shift assay. However, in this system, the known transcription factor can be detected, but it is impossible to detect an unknown protein. In the proteome analyses at present, it is a very important proposition to detect the unknown protein. Thus, it seems to be highly useful to develop the technology of detecting the protein using the transcription chip. In this section, the development of detection method of the transcription factor using MALDI-TOF MS mass spectrometric system will be reported.

a. Peptide Mass Fingerprint (PMF) of NFκB by On-Chip Digestion

It is generally difficult to digest with trypsin on the chip. Causes thereof include inactivation of the enzyme on the hydrophobic surface, masking the substrate site due to steric hindrance, and the like. However, the double-stranded DNA are dissociated at a low salt concentration on the transcription chip, and thus DNA-protein interaction is lost at a low salt concentration to easily liberate the protein in the enzyme reaction solution. Also, the chip surface appears to exhibit hydrophilicity because the DNA are covalently bound thereto. Therefore, the transcription chip appeared to be the ideal chip for the on-chip digestion. After 2 pmol/chip of NFκB was added and reacted, the on-chip trypsin digestion was performed. Subsequently, the peptides present on the chip were purified by Zip Tip purification chip, and detected by an MALDI plate or directly detected from the transcription chip.

Figure 13:
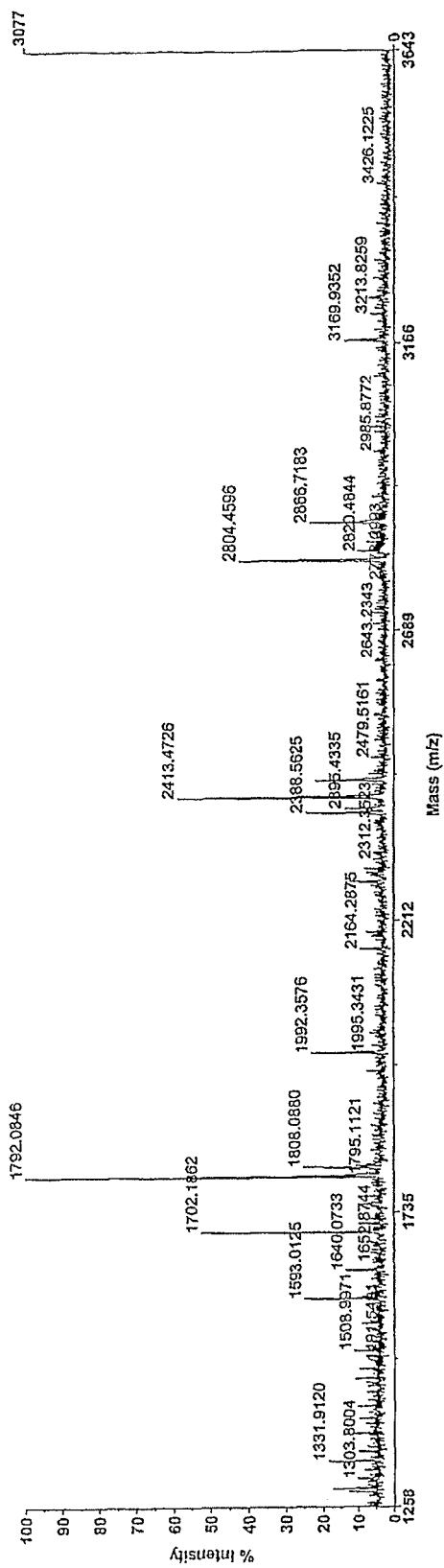
FIG. 13 shows a peptide map of NFκB by on-chip digestion.
Figure 14:
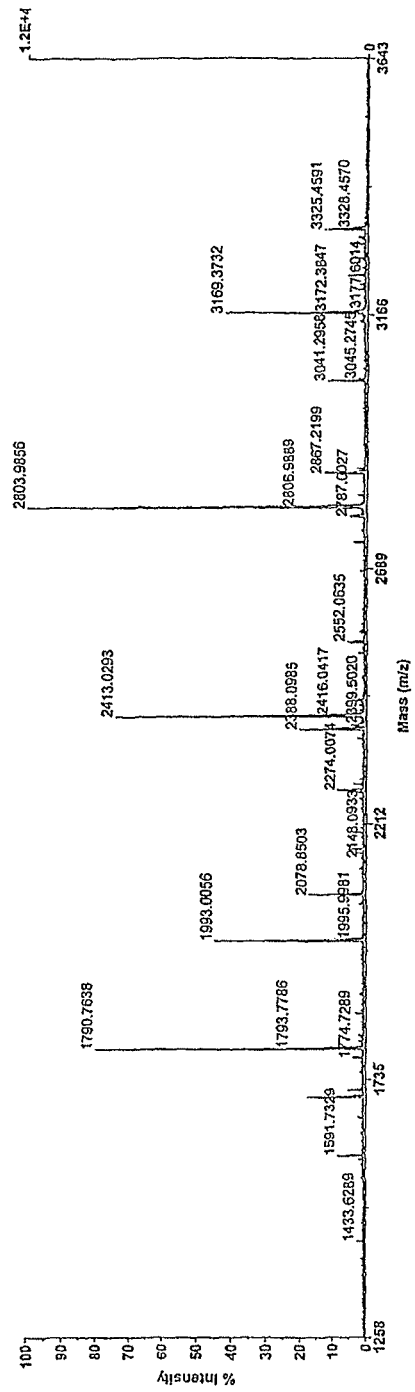
FIG. 14 shows a peptide map of NFκB obtained by trypsin digestion in a solution.

As a result, an ideal peptide map was observed when the trypsin digestion was performed on the chip, the peptides were purified by Zip Tip, and the sample was added to the MALDI plate (FIG. 13). This well conformed to the peptide map observed by digesting NFκB in a solution with trypsin (4 μg/mL) (FIG. 14). Database search was performed by MS-FIT Search based on this peptide mass fingerprint information, and consequently, NFκB was hit at a very high score. Therefore, it was confirmed that many peptides derived from NFκB were captured (FIG. 15).

b. Detection and Identification of Vitamin D Receptor (VDR) by PMF Method

Figure 16:
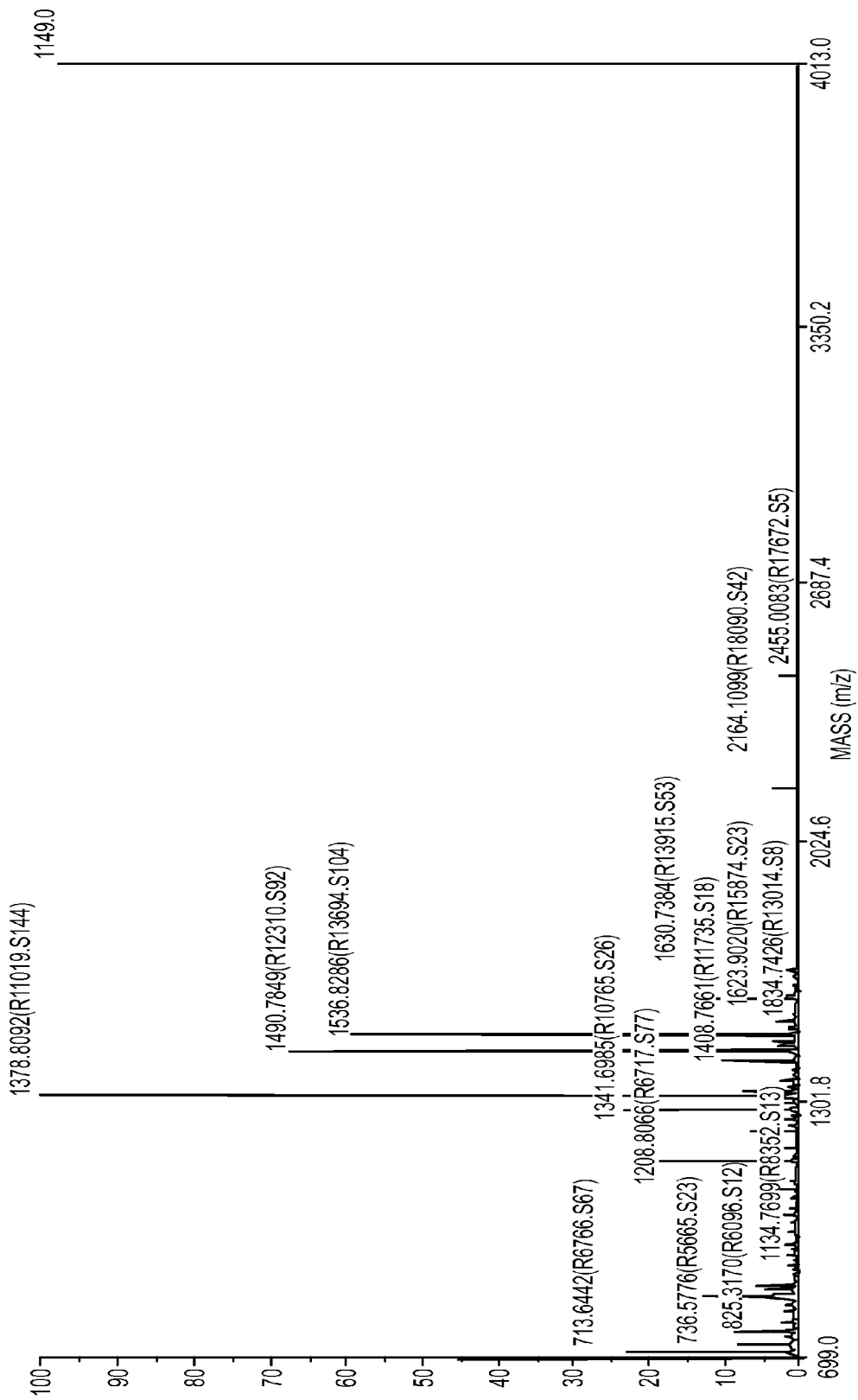
FIG. 16 shows results of the on-chip digestion.
Figure 17:
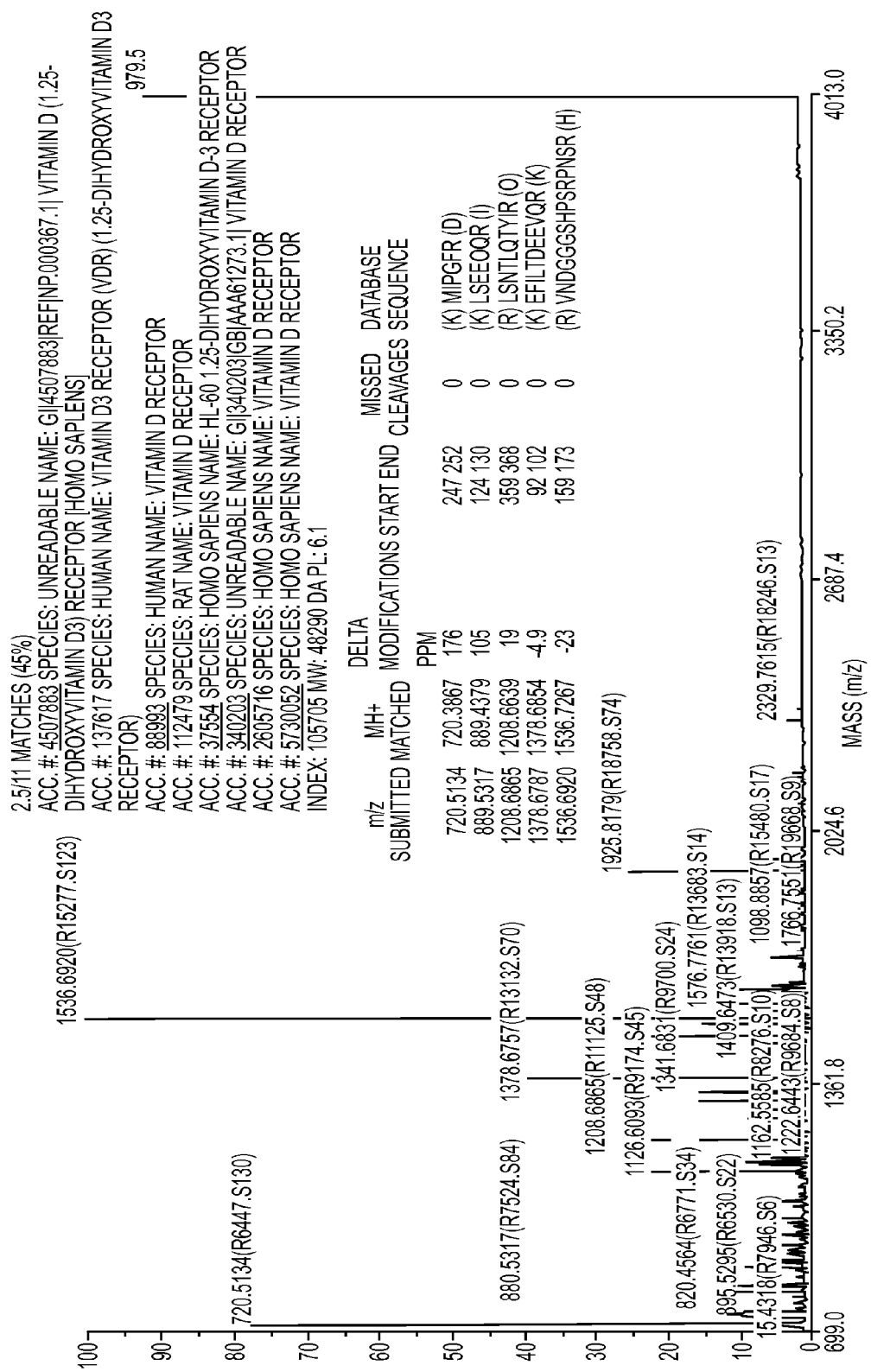
FIG. 17 shows VDR peptide mass fingerprint obtained by trypsin digestion in a solution.

Next, the on-chip digestion of 500 fmol/chip of vitamin D receptor was performed using trypsin (1 μg/mL) on the chip on which the element sequence VDRE which was the recognition sequence of the vitamin D receptor had been immobilized. Subsequently, the sample was added to the MALDI plate, and consequently, the same peptide map as that obtained by trypsin digestion of the sample in the solution was obtained as is the case with NFκB (FIGS. 16 and 17).

Figure 18:
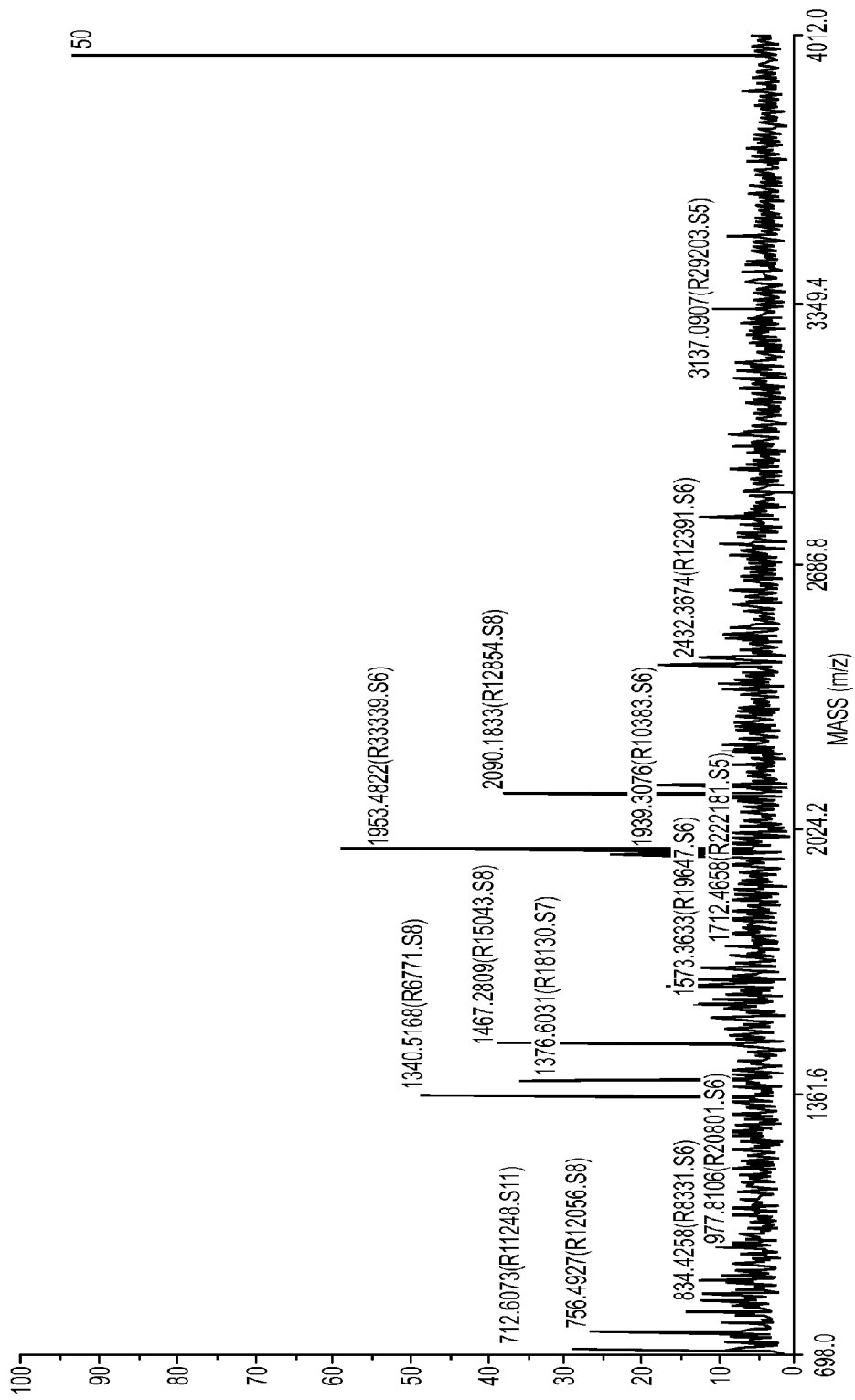
FIG. 18 shows results of direct detection of VDR from the transcription chip of the present invention.

Meanwhile, it was examined whether the peptide map could be directly observed or not by directly irradiating the laser on the transcription chip. As a result, the peptide map of VDR could be directly observed on the chip (FIG. 18).

c. Identification of Transcription Factor by Tandem Mas Spectrum Analysis

The peptide mass fingerprint (PMF) method is used for the identification of the protein contained in the sample by mass spectrometry, but it is difficult to identify the objective protein contained in the sample when the number of spectral peaks obtained is low. Thus, when the objective protein is identified in the sample containing much impurities, the identification by tandem mass spectrum analysis is often performed. However, the tandem mass spectrum analysis has been generally inferior in sensitivity compared to the peptide mass fingerprint method.

Figure 21A:
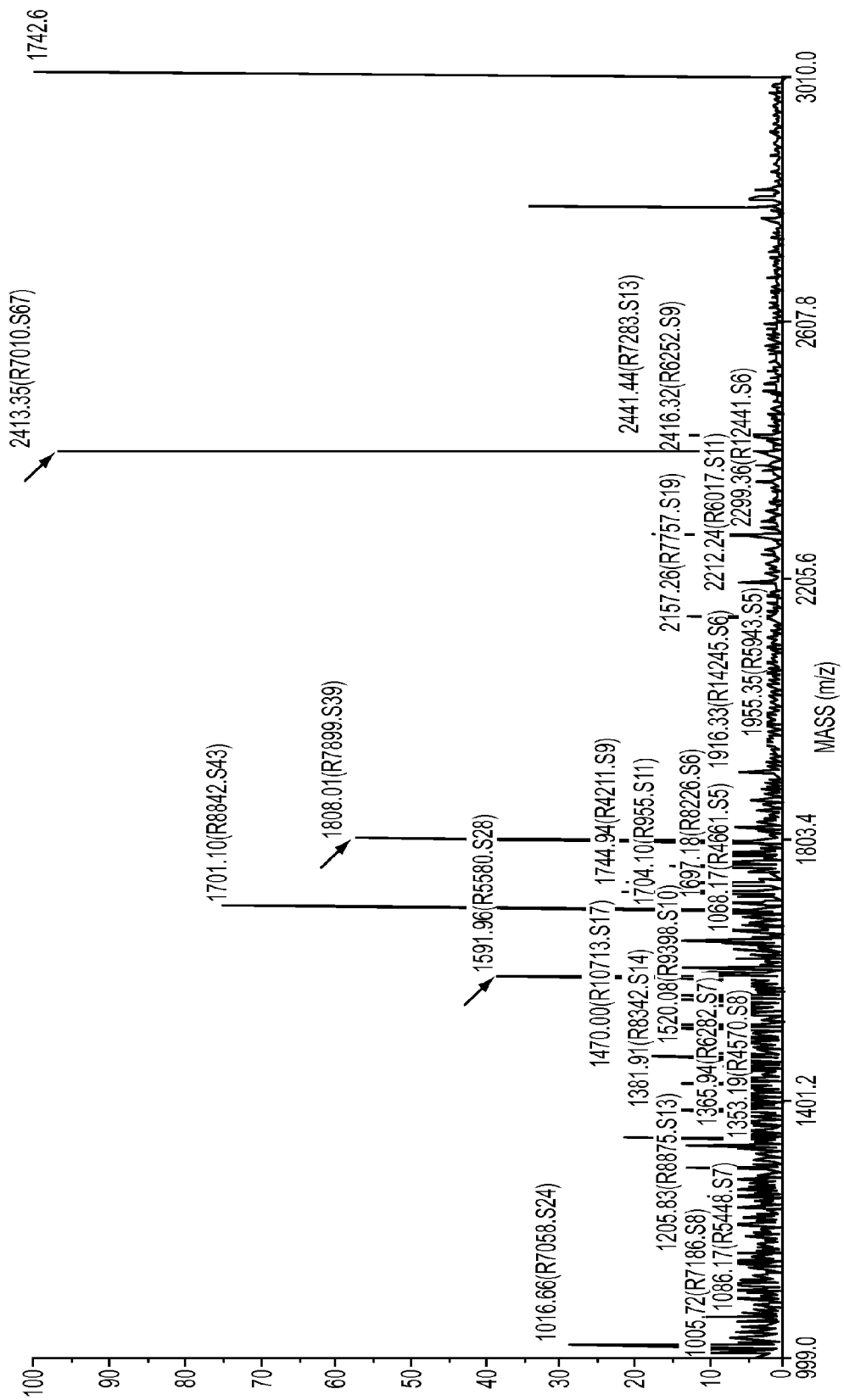
FIG. 21 shows peptide mass fingerprint of NFκB (A) and secondary spectra 1701.10 m/z (B), 1808.01 m/z (C), and 2413.35 m/z (D).
Figure 21B:
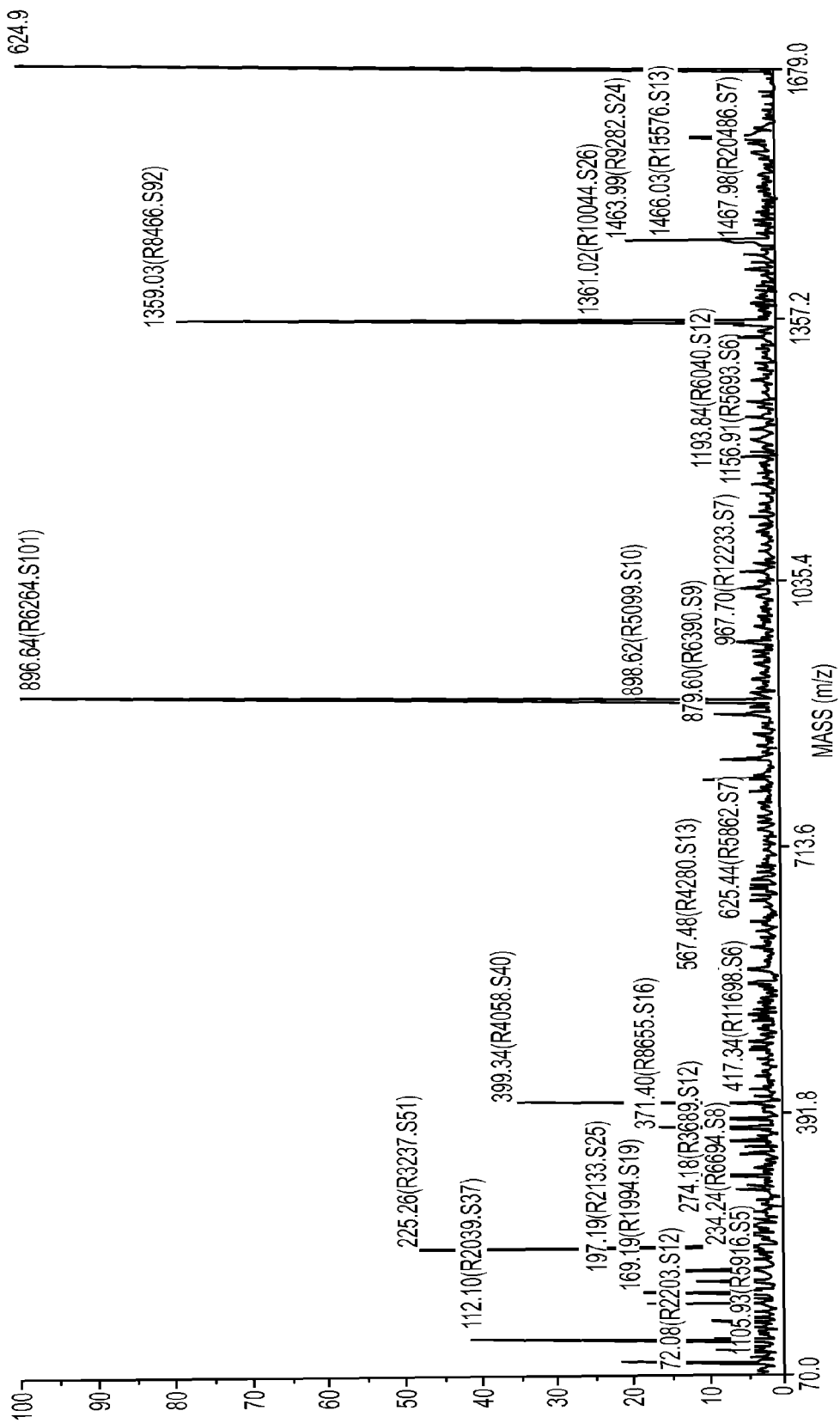
Figure 21C:
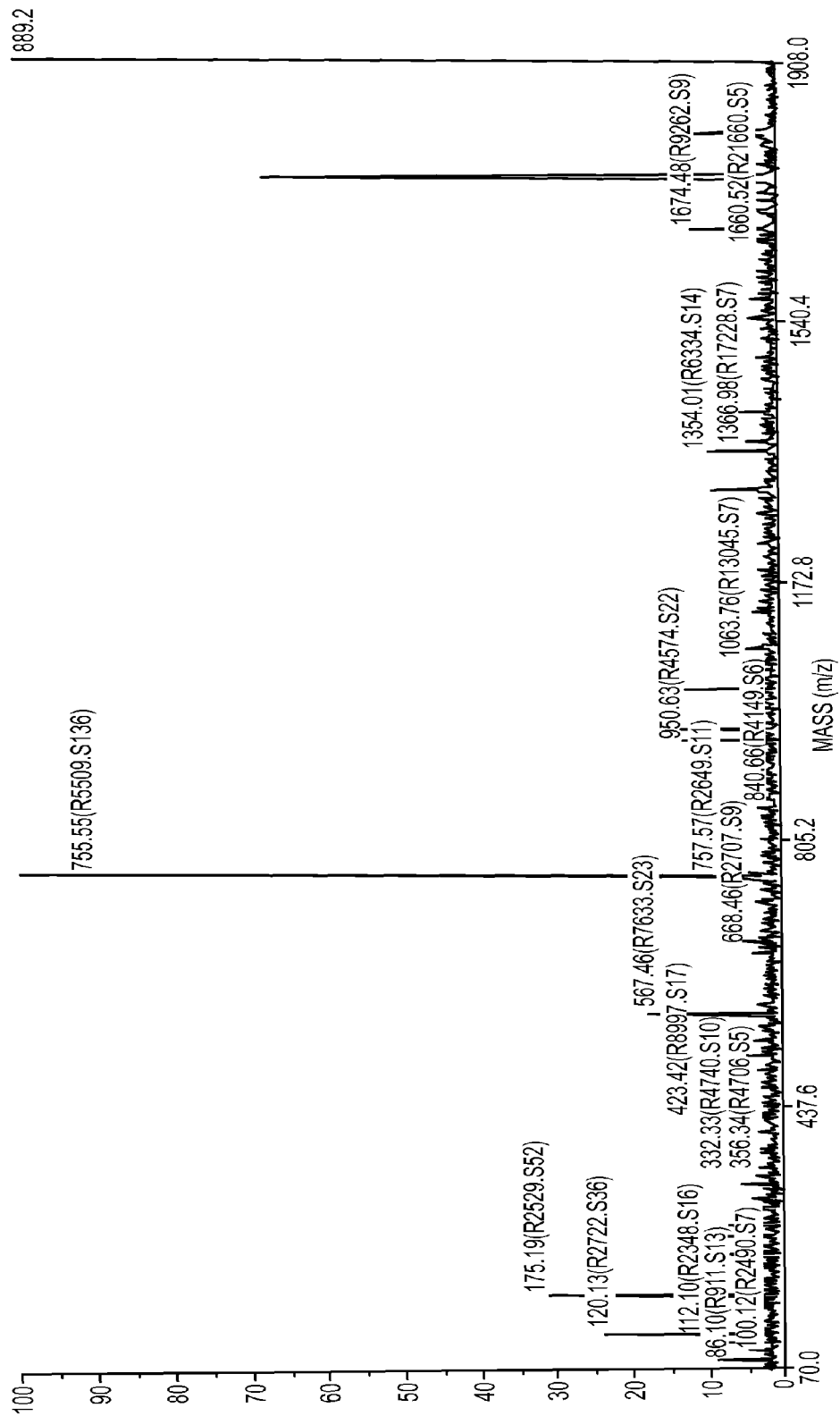
Figure 21D:
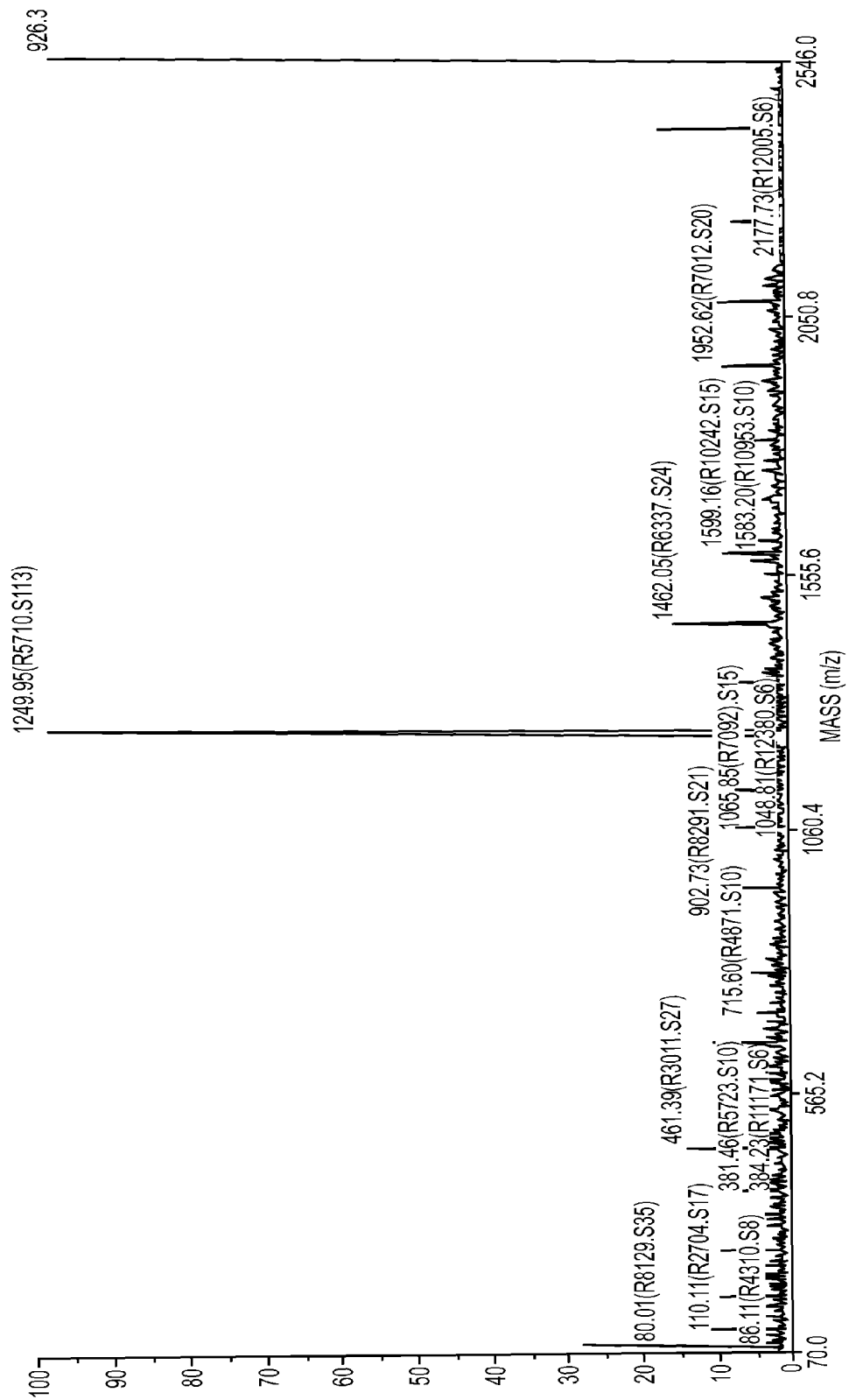

For the peaks of 1701.10 m/z, 1808.01 m/z and 2413.35 m/z from the peptide mass fingerprint (FIG. 21A) obtained by calibrating the mass from the transcription chip to which NFκB had been immobilized, the tandem mass analysis was performed (FIGS. 21B, C and D). A secondary spectrum could be obtained for each peak, and thus, these analysis results were applied to MASCOT database search. As a result, all of the peptides well conformed to mass data of NFκB in the database (FIG. 22). The above results suggest that the transcription chip can efficiently capture NFκB through the element DNA and consequently the tandem mass analysis can be applied.

(4) Applicability of the Present Invention (A) Quantitative Detection of Transcription Factor with High Sensitivity Using Transcription Chip It is the first large subject of this study that an experimental system with high sensitivity and specificity is constructed to establish a high sensitive quantitative detection system by allowing the chip (transcription chip) where the element sequence has been immobilized on the DLC chip or GeneDia™ to capture the protein (transcription factor). For solving this subject, it has been important to make the DNA-immobilized chip having a high capturing capacity of the transcription factor and establish an assay system in which non-specific binding of the transcription factor and the antibody can be minimized. The above subject was responded by examining binding reaction conditions such as blocking condition and examining the immobilized DNA sequences.

For the recognition sequence (element sequence) of the transcription factor NFκB, the results in which the location in the immobilized double-stranded DNA seemed to be more important than the copy number were obtained (FIG. 5). The capacity of capturing NFκB was higher in the case of locating the element sequence closer to a liquid layer in the immobilized double-stranded DNA. It was suggested that the inner recognition sequence located far from the surface side of the oligonucleotide hardly formed the transcription factor-antibody complex due to steric hindrance. Therefore as the general method for realizing the highly sensitive detection, it was suggested that it was important for the capacity of capturing the transcription factor to design the element sequence close to the surface side (opposite side to the immobilized site) of the double-stranded oligonucleotide. It was revealed that both the oligonucleotide and the PCR product could be immobilized as the immobilized DNA. Thus, a transcription initiation complex in a certain gene region will become possible in the future by acquiring the certain gene region by PCR and immobilizing in addition to ordinary assays using the oligonucleotides.

The investigation of the blocking condition was important for decreasing non-specific bindings in the assay. The BSA concentration at 1% in the binding buffer was the optimal condition. When the experimental system was constructed, increased assay values in the negative controls probably due to the effect of non-specific bindings were often observed, but the experimental system with high reproducibility could be constructed by using the tris buffer and prolonging the blocking time period (4° C., O/N) (FIG. 7).

As a result of examining the above, eventually, the detection limit down to 0.33 ng/mL and 1.00 ng/mL were obtained for the case using GeneDia™ and the case using the DLC chip, respectively. Using HeLa cells, it became possible to perform profiling of inflammatory transcription factors activated by the stimulation with TNFα and PMA at protein levels.

(B) Detection of Transcription Factor Using Highly Integrated (Microarrayed) Double-Stranded DNA Chip As the intended use for small scale studies, the conventional technology has accomplished profiling and quantification of the transcription factors. However, considering the throughput property and consumed quantity as a supporting system for diagnosis and drug discovery in the light of proteome analyses in the future, the conventional technology has not actually come into practical use.

As shown in the present results of the on-chip ELISA, a quantitative measurement on a size of 3 mm×3 mm was enabled. Thus, it is possible to perform the quantitative and highly sensitive measurement on the size of approximately two glass slides equivalent to that in one 96-well microplate.

Furthermore, in the on-chip fluorescence immunoassay, it could be monitored that NFκB was specifically bound to the PRD II sequence on the chip onto which nine spots of the double-stranded DNA had been immobilized at a size of 3 mm×3 mm by making the transcription chip having the microarrayed double-stranded DNA (FIG. 12).

(C) Detection and Identification of Transcription Factor Using MALDI-TOF MS

It becomes possible to detect and identify the unknown protein or analyze post-translational modification, which cannot be detected by ELISA, by detecting the protein using the mass spectrometer.

At present, a protein chip system using SELDI-TOF MS from Ciphergen is commercially available, and the protein chip to which the antibody has been immobilized using this system has been developed, but it is not sufficient in terms of throughput property and accuracy of mass analysis.

Meanwhile, with respect to the transcription chip to which the DNA has been immobilized, generally, the molecular weights of the transcription factors are often about 50,000, and it has been difficult to identify from the mass information by the current accuracy of the mass spectrometer. Thus, it was speculated that if a system using a diamond (DLC) chip capable of immobilizing the DNA at high density and MALDI-TOF MS using the peptide mass fingerprint method by trypsin digestion was used, the mass information of the transcription factor molecule could be directly acquired from the chip, and the detection system was made. As a result, the transcription factor could be detected and identified directly on the chip for the first time (FIG. 18). In addition, by combining with the tandem mass spectrum analysis, it became possible to detect and identify the transcription factor captured on the chip (FIG. 21).

According to the present invention, the profiling of many transcription factors is realized by the on-chip ELISA using the highly sensitive transcription chip, it is possible to sensitively detect and quantify the transcription factor in the culture cell extract and the tissue, and it is possible to use the above as tools for screening, predicting the toxicity at the drug discovery or diagnostic information.

Also, it is possible to directly identify the transcription factor on the chip using the peptide mass fingerprint method. Furthermore, the tandem mass spectrum analysis was possible, and thus, it is possible to identify the transcription factor in the sample comprising the impurities.

Figure 19:
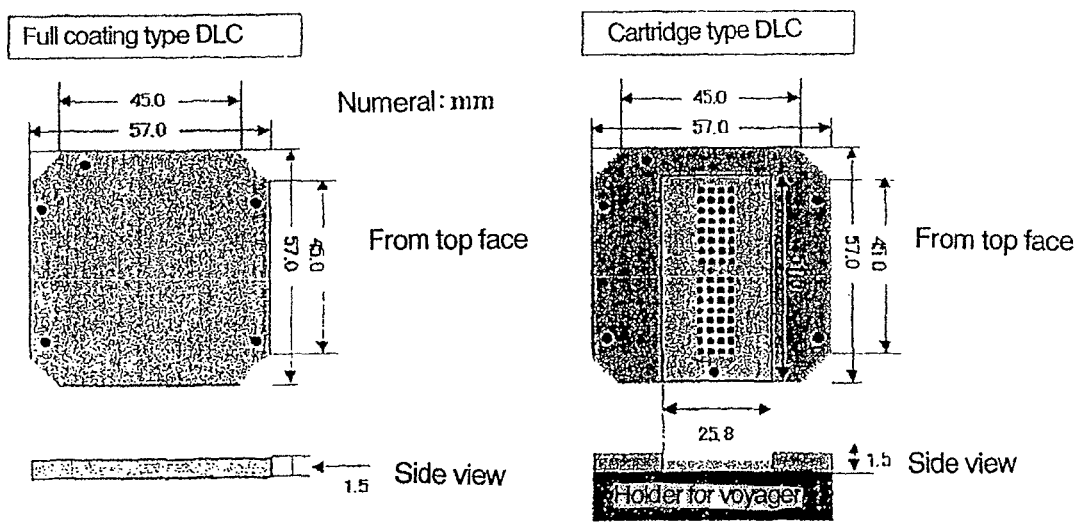
FIG. 19 shows one example of a DLC plate for MALDI-TOF MS.

It is possible to detect and identify the transcription factor with keeping sensitivity and accuracy equivalent to or more than those of the conventional MALDI plate by the use of the transcription chip (FIG. 19) corresponding to a focus position of ionized laser.

According to the present invention, it is possible to efficiently profile the transcription factor.

The invention claimed is:

1. A method for assaying a binding of a mammalian transcription factor comprising a step of interacting a sample capable of comprising the transcription factor with the transcription chip wherein the transcription chip comprises:
   at least one polynucleotide comprising one or more element sequences to which a mammalian transcription factor can be bound is immobilized on a substrate;
   wherein the one or more element sequences is selected from the group consisting of GGAATTTCCC (SEQ ID NO. 23) and GGGAAATTCC (SEQ ID NO. 24); GGGGATCCC and GGGATCCCC; TGACTCAT and ATGAGTCA; AGGTCA and TGACCT; AGGTCA and TGACCT; AGGTCA and TGACCT; AGGTCATGACCT (SEQ ID NO. 25); AGAACA and TGTTCT; TGACGTCA;
   wherein said polynucleotide has a partial sequence of a promoter;
   wherein said substrate is made by forming a diamond thin film on a support;
   wherein said polynucleotide is bound to the diamond thin film through an optionally appropriate spacer; and
   detecting the transcription factor bound to the transcription chip.

2. The method according to claim 1 for evaluating an effect of a subject substance on the transcription factor, wherein said sample is a cell lysate of cells cultured in the presence of the subject substance.

3. The method according to claim 2 wherein the binding of the transcription factor is detected by an antibody against the transcription factor or a method utilizing mass spectrometry.

4. The method according to claim 3 wherein the detection using the antibody is an ELISA and the method utilizing mass spectrometry is a peptide mass fingerprint method.

5. The method according to claim 1, wherein at least two polynucleotides comprising one or more element sequences to which transcription factors can be bound respectively are immobilized on the substrate.

6. The method according to claim 1, wherein the at least one polynucleotide is hybridized with a complementary polynucleotide to form a double-stranded DNA.

7. The method according to claim 1, wherein the sample is a cell lysate.

8. The method according to claim 7, wherein the cell lysate is of mammalian cells.

9. The method according to claim 1, wherein the transcription factor is human.

10. The method according to claim 1, wherein the one or more element sequences binds a mammalian transcription factor.

11. The method according to claim 1, wherein the binding of the transcription factor is detected utilizing a peptide mass fingerprint method.

12. The method according to claim 7, wherein the binding of the transcription factor is detected utilizing a peptide mass fingerprint method.

* * * * *

SEQUENCE LISTING

```
<160> NUMBER OF SEQ ID NOS: 25

<210> SEQ ID NO 1
<211> LENGTH: 26
<212> TYPE: DNA
<213> ORGANISM: Artificial Sequence
<220> FEATURE:
<223> OTHER INFORMATION: Transcription Factor

<400> SEQUENCE: 1
cctcacagtt tgtaaatctt tttccc                                  26

<210> SEQ ID NO 2
<211> LENGTH: 25
<212> TYPE: DNA
<213> ORGANISM: Artificial Sequence
<220> FEATURE:
<223> OTHER INFORMATION: Transcription Factor

<400> SEQUENCE: 2
ggcctattta tatgagatgg tcctc                                   25

<210> SEQ ID NO 3
<211> LENGTH: 24
<212> TYPE: DNA
<213> ORGANISM: Artificial Sequence
<220> FEATURE:
<223> OTHER INFORMATION: Transcription Factor

<400> SEQUENCE: 3
agaggaattt cccactttca cttc                                    24

<210> SEQ ID NO 4
<211> LENGTH: 44
<212> TYPE: DNA
<213> ORGANISM: Artificial Sequence
<220> FEATURE:
<223> OTHER INFORMATION: Transcription Factor
```

```
<400> SEQUENCE: 4
gggagctgag tagggaaatt ccatgcatgc gggaaattcc catg                        44

<210> SEQ ID NO 5
<211> LENGTH: 44
<212> TYPE: DNA
<213> ORGANISM: Artificial Sequence
<220> FEATURE:
<223> OTHER INFORMATION: Transcription Factor

<400> SEQUENCE: 5
catgggaatt tcccgcatgc atggaatttc cctactcagc tccc                        44

<210> SEQ ID NO 6
<211> LENGTH: 44
<212> TYPE: DNA
<213> ORGANISM: Artificial Sequence
<220> FEATURE:
<223> OTHER INFORMATION: Transcription Factor

<400> SEQUENCE: 6
catgggaatt tcccgcatgc atggaatttc cctactcagc tccc                        44

<210> SEQ ID NO 7
<211> LENGTH: 42
<212> TYPE: DNA
<213> ORGANISM: Artificial Sequence
<220> FEATURE:
<223> OTHER INFORMATION: Transcription Factor

<400> SEQUENCE: 7
gggagctgag tagggatcc catgcatgcg gggatcccca tg                           42

<210> SEQ ID NO 8
<211> LENGTH: 42
<212> TYPE: DNA
<213> ORGANISM: Artificial Sequence
<220> FEATURE:
<223> OTHER INFORMATION: Transcription Factor

<400> SEQUENCE: 8
catggggatc cccgcatgca tgggatcccc tactcagctc cc                          42

<210> SEQ ID NO 9
<211> LENGTH: 40
<212> TYPE: DNA
<213> ORGANISM: Artificial Sequence
<220> FEATURE:
<223> OTHER INFORMATION: Transcription Factor

<400> SEQUENCE: 9
gggagctgag tatgactcat atgcatgctg actcatcatg                             40

<210> SEQ ID NO 10
<211> LENGTH: 40
<212> TYPE: DNA
<213> ORGANISM: Artificial Sequence
<220> FEATURE:
<223> OTHER INFORMATION: Transcription Factor

<400> SEQUENCE: 10
catgatgagt cagcatgcat atgagtcata ctcagctccc                             40
```

```
<210> SEQ ID NO 11
<211> LENGTH: 54
<212> TYPE: DNA
<213> ORGANISM: Artificial Sequence
<220> FEATURE:
<223> OTHER INFORMATION: Transcription Factor

<400> SEQUENCE: 11
gggagctgag taaggtcaag gaggtcaatg catgcaggtc aaggaggtca catg       54

<210> SEQ ID NO 12
<211> LENGTH: 54
<212> TYPE: DNA
<213> ORGANISM: Artificial Sequence
<220> FEATURE:
<223> OTHER INFORMATION: Transcription Factor

<400> SEQUENCE: 12
catgtgacct ccttgacctg catgcattga cctccttgac cttactcagc tccc       54

<210> SEQ ID NO 13
<211> LENGTH: 58
<212> TYPE: DNA
<213> ORGANISM: Artificial Sequence
<220> FEATURE:
<223> OTHER INFORMATION: Transcription Factor

<400> SEQUENCE: 13
gggagctgag taaggtcacc aggaggtcaa tgcatgcagg tcaccaggag gtcacatg   58

<210> SEQ ID NO 14
<211> LENGTH: 58
<212> TYPE: DNA
<213> ORGANISM: Artificial Sequence
<220> FEATURE:
<223> OTHER INFORMATION: Transcription Factor

<400> SEQUENCE: 14
catgtgacct cctggtgacc tgcatgcatt gacctcctgg tgaccttact cagctccc   58

<210> SEQ ID NO 15
<211> LENGTH: 54
<212> TYPE: DNA
<213> ORGANISM: Artificial Sequence
<220> FEATURE:
<223> OTHER INFORMATION: Transcription Factor

<400> SEQUENCE: 15
gggagctgag taaggtcaca gtgacctatg catgcaggtc acagtgacct catg       54

<210> SEQ ID NO 16
<211> LENGTH: 50
<212> TYPE: DNA
<213> ORGANISM: Artificial Sequence
<220> FEATURE:
<223> OTHER INFORMATION: Transcription Factor

<400> SEQUENCE: 16
tcaggtcaca gtgacctgat ctcaggtcac agtgaccttt cacgaggtac             50

<210> SEQ ID NO 17
<211> LENGTH: 48
<212> TYPE: DNA
<213> ORGANISM: Artificial Sequence
<220> FEATURE:
<223> OTHER INFORMATION: Transcription Factor
```

```
<400> SEQUENCE: 17
gggagctgag taaggtcatg acctatgcat gcaggtcatg acctcatg                48

<210> SEQ ID NO 18
<211> LENGTH: 48
<212> TYPE: DNA
<213> ORGANISM: Artificial Sequence
<220> FEATURE:
<223> OTHER INFORMATION: Transcription Factor

<400> SEQUENCE: 18
catgaggtca tgacctgcat gcataggtca tgaccttact cagctccc                 48

<210> SEQ ID NO 19
<211> LENGTH: 54
<212> TYPE: DNA
<213> ORGANISM: Artificial Sequence
<220> FEATURE:
<223> OTHER INFORMATION: Transcription Factor

<400> SEQUENCE: 19
gggagctgag taagaacact gtgttctatg catgcagaac actgtgttct catg          54

<210> SEQ ID NO 20
<211> LENGTH: 54
<212> TYPE: DNA
<213> ORGANISM: Artificial Sequence
<220> FEATURE:
<223> OTHER INFORMATION: Transcription Factor

<400> SEQUENCE: 20
catgagaaca gactgttctg catgcataga acagactgtt cttactcagc tccc          54

<210> SEQ ID NO 21
<211> LENGTH: 40
<212> TYPE: DNA
<213> ORGANISM: Artificial Sequence
<220> FEATURE:
<223> OTHER INFORMATION: Transcription Factor

<400> SEQUENCE: 21
gggagctgag tatgacgtca atgcatgctg acgtcacatg                          40

<210> SEQ ID NO 22
<211> LENGTH: 40
<212> TYPE: DNA
<213> ORGANISM: Artificial Sequence
<220> FEATURE:
<223> OTHER INFORMATION: Transcription Factor

<400> SEQUENCE: 22
catgtgacgt cagcatgcat tgacgtcata ctcagctccc                          40

<210> SEQ ID NO 23
<211> LENGTH: 10
<212> TYPE: DNA
<213> ORGANISM: Artificial Sequence
<220> FEATURE:
<223> OTHER INFORMATION: Transcription Factor Element Sequence

<400> SEQUENCE: 23
ggaatttccc                                                           10
```

```
<210> SEQ ID NO 24
<211> LENGTH: 10
<212> TYPE: DNA
<213> ORGANISM: Artificial Sequence
<220> FEATURE:
<223> OTHER INFORMATION: Transcription Factor Element Sequence

<400> SEQUENCE: 24
gggaaattcc                                                              10

<210> SEQ ID NO 25
<211> LENGTH: 12
<212> TYPE: DNA
<213> ORGANISM: Artificial Sequence
<220> FEATURE:
<223> OTHER INFORMATION: Transcription Factor Element Sequence

<400> SEQUENCE: 25
aggtcatgac ct                                                           12
```